United States Patent
Rodriguez Gonzalez et al.

(10) Patent No.: US 10,796,799 B2
(45) Date of Patent: Oct. 6, 2020

(54) METHODS FOR THE PREDICTION OF A PERSONALIZED ESA-DOSE IN THE TREATMENT OF ANEMIA

(71) Applicants: DEUTSCHES KREBSFORSCHUNGSZENTRUM STIFTUNG DES ÖFFENTLICHEN RECHTS, Heidelberg (DE); ALBERT-LUDWIGS-UNIVERSITAT FREIBURG, Freiburg (DE)

(72) Inventors: Agustin Rodriguez Gonzalez, Heidelberg (DE); Marcel Schilling, Heidelberg (DE); Ursula Klingmueller, Heidelberg (DE); Andreas Raue, Cambridge, MA (US); Max Schelker, Berlin (DE); Jens Timmer, Freidburg (DE); Michael Jarsch, Bad Heilbrunn (DE); Bernhard Steiert, Freiburg (DE)

(73) Assignees: DEUTSCHES KREBSFORSCHUNGSZENTRUM STIFTUNG DES ÖFFENTLICHEN RECHTS, Heidelberg (DE); ALBERT-LUDWIGS-UNIVERSITAT FREIBURG, Freiburg (DE)

( * ) Notice: Subject to any disclaimer, the term of this patent is extended or adjusted under 35 U.S.C. 154(b) by 677 days.

(21) Appl. No.: 15/319,073

(22) PCT Filed: Jun. 18, 2015

(86) PCT No.: PCT/EP2015/063775
§ 371 (c)(1),
(2) Date: Dec. 15, 2016

(87) PCT Pub. No.: WO2015/193462
PCT Pub. Date: Dec. 31, 2005

(65) Prior Publication Data
US 2017/0128532 A1    May 11, 2017

(30) Foreign Application Priority Data
Jun. 18, 2014   (EP) .................................. 14173054

(51) Int. Cl.
*G16H 50/20* (2018.01)
*G16H 50/50* (2018.01)
(Continued)

(52) U.S. Cl.
CPC .......... *G16H 50/20* (2018.01); *A61K 9/0019* (2013.01); *A61K 38/1816* (2013.01);
(Continued)

(58) Field of Classification Search
None
See application file for complete search history.

(56) References Cited

FOREIGN PATENT DOCUMENTS

WO    WO-2009089039 A1 *   7/2009    ......... A61B 5/02035
WO    WO 2011/082421         7/2011

OTHER PUBLICATIONS

Becker et al, "Covering a Broad Dynamic Range: Information Processing at the Erythropoietin Receptor", *Science*, 328(5984):1404-1408 (2010).
(Continued)

*Primary Examiner* — Olivia M. Wise
(74) *Attorney, Agent, or Firm* — Foley Hoag LLP

(57) ABSTRACT

An integrative pharmacokinetic/pharmacodynamics (PK/PD) ESA-EpoR mathematical model calculates the binding behavior of erythropoiesis stimulating agents (ESA). The invention provides methods for the determining of ESA binding sites in cells or patients suffering from anemia. Knowing the amount of ESA binding sites enables the clinical practitioner to optimize the dosage regimen during a treatment of anemia, in particular in patients suffering from a cancerous disease. Further provided are methods for
(Continued)

Figure 1A:
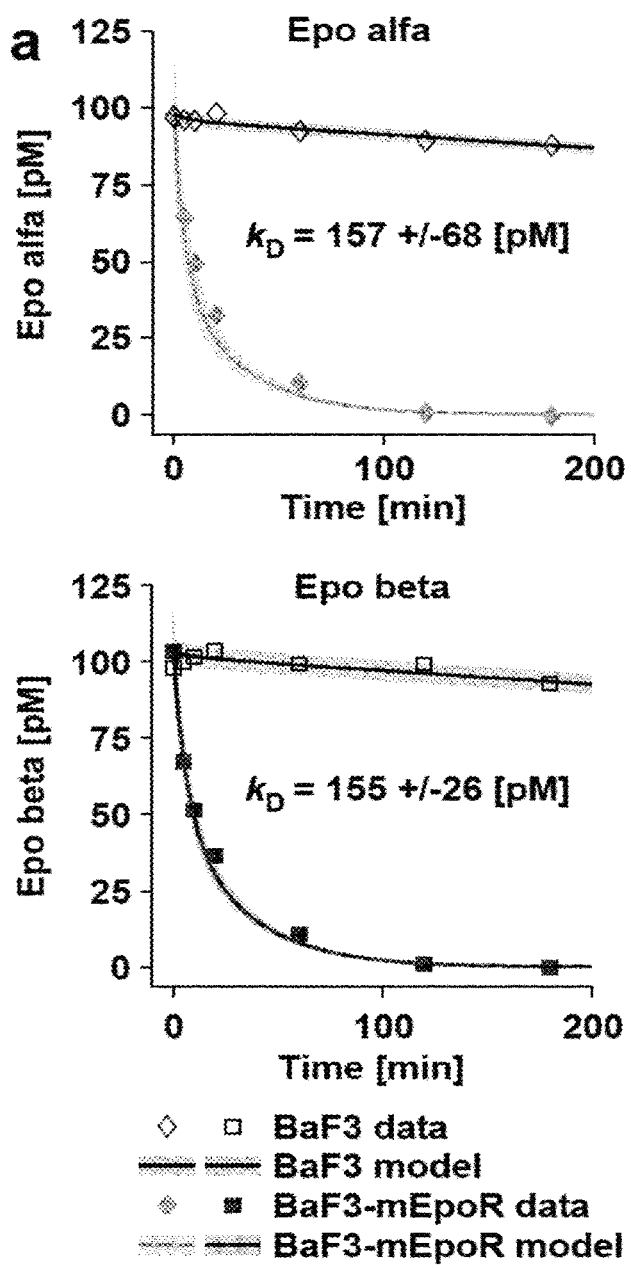

screening ESAs which have a higher specificity for cells strongly expressing the EPO receptor such as colony forming units-erythroid (CFU-E) cells, and not to cells with a low level of EPO receptor cell surface expression, which is the case in cancer cells. Also provided is a computer implemented method, comprising the use of the mathematical model of the invention.

8 Claims, 14 Drawing Sheets

(51) Int. Cl.
G16B 5/00 (2019.01)
G01N 33/50 (2006.01)
G01N 33/68 (2006.01)
G01N 33/80 (2006.01)
A61K 38/18 (2006.01)
A61K 9/00 (2006.01)
G01N 33/72 (2006.01)

(52) U.S. Cl.
CPC ..... *G01N 33/5044* (2013.01); *G01N 33/6893* (2013.01); *G01N 33/721* (2013.01); *G01N 33/80* (2013.01); *G16B 5/00* (2019.02); *G16H 50/50* (2018.01); *G01N 2800/222* (2013.01)

(56) References Cited

OTHER PUBLICATIONS

Bellazzi et al., "Drug Delivery Optimization Through Bayesian Networks: An Application to Erythropoietin Therapy in Uremic Anemia", *Computers and Biomedical Research*, 26(3):274-293 (1993).

Notification of Transmittal of the International Search Report and the Written Opinion of the International Searching Authority, International Application No. PCT/EP2015/063775, entitled "Methods For The Prediction of A Personalized ESA-Dose in the Treatment of Anemia", dated Jan. 22, 2016.

Notification Concerning Transmittal of International Preliminary Report on Patentability, International Application No. PCT/EP2015/063775, entitled "Methods For The Prediction of A Personalized ESA-Dose in the Treatment of Anemia", dated Dec. 29, 2016.

* cited by examiner

FIG. 3A
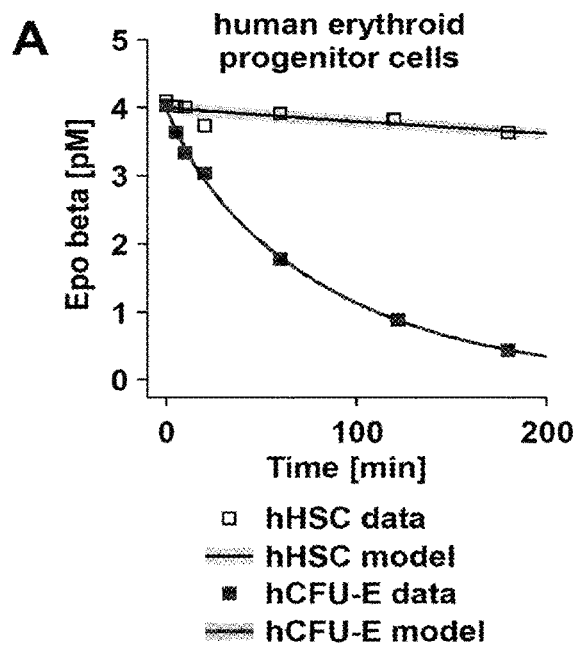
FIG. 3B
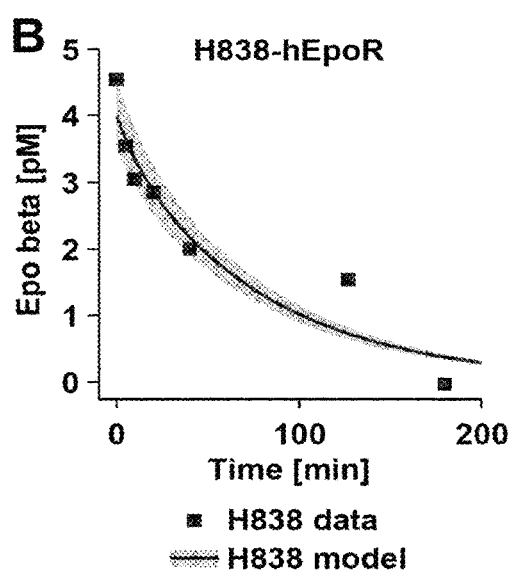
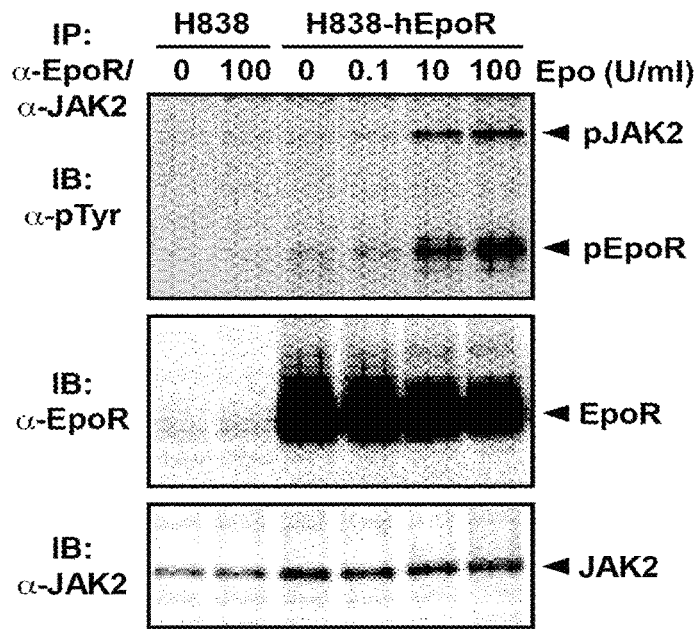
FIG. 3C

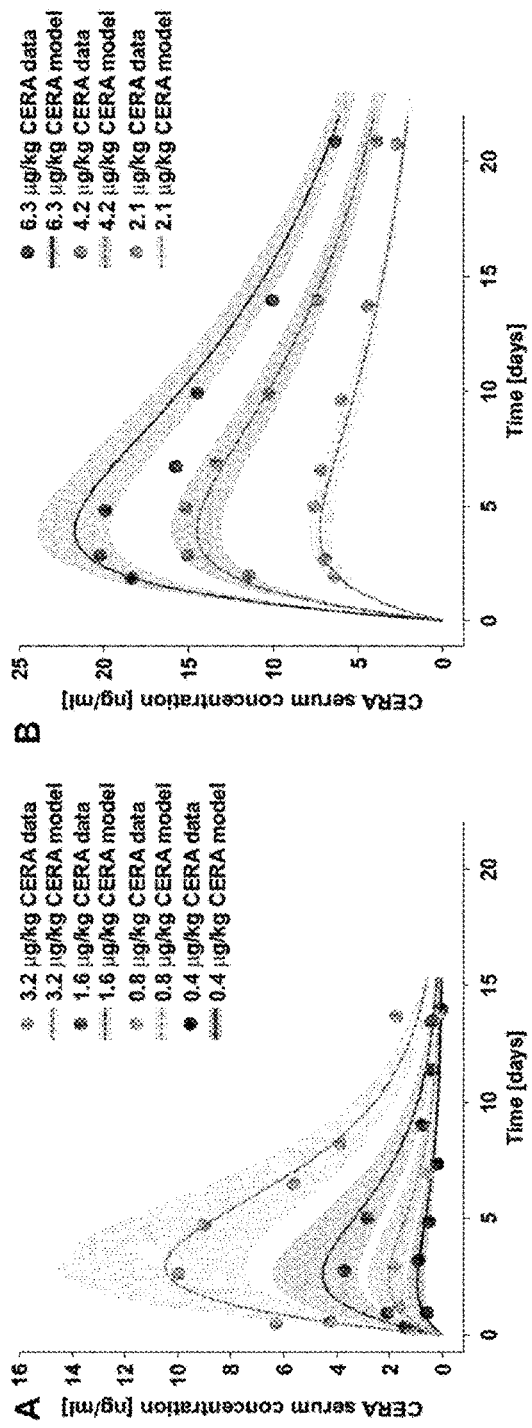
FIG. 5B
FIG. 5A
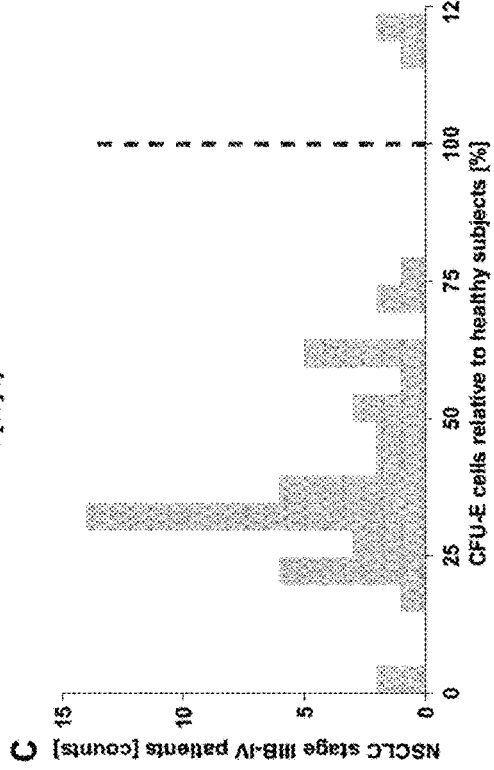
FIG. 5C

FIG. 6A
FIG. 6B
a) *in vitro* trafficking model
b) *in vivo* PK/PD model
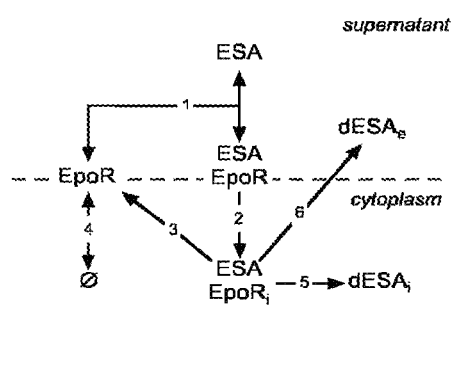
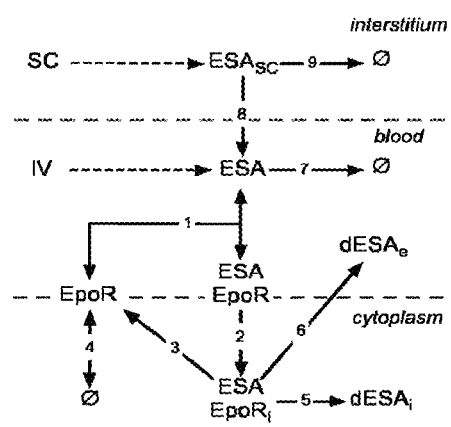
c) *in vivo* PK/PD model
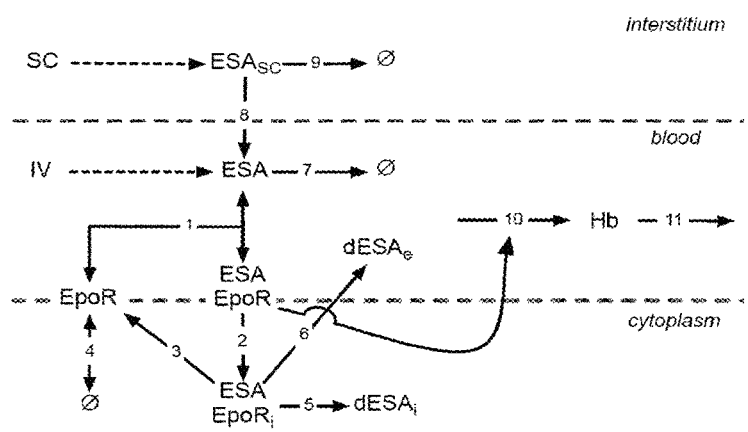
FIG. 6C

METHODS FOR THE PREDICTION OF A PERSONALIZED ESA-DOSE IN THE TREATMENT OF ANEMIA

RELATED APPLICATIONS

This application is the U.S. National Stage of International Application No. PCT/EP2015/063775, filed Jun. 18, 2015, which designates the U.S., published in English, and claims priority under 35 U.S.C. §§ 119 or 365(c) to European Application No. 14173054.9, filed on Jun. 18, 2014. The entire teachings of the above application are incorporated herein by reference.

FIELD OF THE INVENTION

The present invention pertains to the use of an Integrative pharmacokinetic/pharmacodynamics (PK/PD) ESA-EpoR mathematical model for calculating the binding behaviour of erythropoiesis stimulating agents (ESA). The invention provides methods for the determining of ESA binding sites in cells or patients suffering from anemia. Knowing the amount of ESA binding sites enables the clinical practitioner to optimize the dosage regimen during a treatment of anemia, in particular in patients suffering from a cancerous disease. Further provided are methods for screening ESAs which have a higher specificity for cells strongly expressing the EPO receptor such as colony forming units-erythroid (CFU-E) cells, and not to cells with a low level of EPO receptor cell surface expression, which is the case in cancer cells. Also provided is a computer implemented method, comprising the use of the mathematical model of the invention.

DESCRIPTION

Lung carcinoma is the most frequent cause of death in cancer with 1.59 million of deaths in 2012, of which 80% were diagnosed as Non-Small Cell Lung Carcinoma (NSCLC). Most of the patients are diagnosed in a stage IIIB or IV and treated with a combination of platinum compounds and taxanes, gemcitabine or vinorelbine as a first line of treatment. In lung carcinoma there is a high prevalence of anemia ([Hb]≤11 g/dL), ranging from 50% to 70%, although in advanced stages it could reach up to 90%. The anemic grade depends on the therapy, tumor stage and duration of the disease. Cancer related anemia reduces the quality of life (Cella et al, 2004) and it is considered a risk factor for mortality in cancer patients (Caro 2001). Furthermore, it has been reported that anemia affects the outcome of the anticancer therapy, diminishing the chemotherapy response in NSCLC patients (Albain 1991, MacRae 2002 and Robnett 2002).

The etiology of anemia in cancer is complex due to the multifactorial causes such as deficiencies in vitamin B12 and folic acid, bleeding, haemolysis, inflammatory cytokines secreted in the tumor context and reduction in the iron uptake (Weiss and Goodnough N. Engl. J Med 2005) are some of the causal origins of cancer related anemia. In adition, platinum-based chemotherapy inhibits the renal production of Epo and exerts myelosuppresion what increases the anemia (Groopman 1999, Kosmidis 2005, Ludwig 2004).

Currently, there are two available therapeutic approaches for the management of anemia in cancer patients: homologous red blood cells (RBC) transfusions or administration of Erythropoiesis Stimulating Agents (ESAs). The first option has an immediate but transient improvement of anemia. The disadvantages of the RBC transfusions are: the potential risk of infectious agent transmission, immunosuppression, hemolysis, allergic reactions, a non-sustained relief of anemia symptoms and the risk of transfusion-related acute lung injury (Klein 2007). Furthermore, the clinical demand of transfusions in lung carcinoma is higher in NSCLC than in other cancers (Barret-Lee 2000), with 40% requiring at least one transfusion, and 22% requiring more than one (Langer 2002, Barret-Lee, Estrin 1999, Skillings 1999).

The second therapeutic alternative is based on the administration of ESAs. This approach increases and sustains the haemoglobin (Hb) levels, reduces the likelihood of RBC transfusions, and improves the quality of life (Meta-analisis cochrane: Tonia, Melter, The Cochrane library 2012). ESA treatments increase the red blood cell (RBC) production by specific activation of erythropoiesis receptor (EpoR) of erythrocytic progenitors in the bone marrow (Egrie 1986, 2003,) (Wu, Liu Lodish, Cell 1995). However, this treatment is not effective in 30% to 40% of patients. The reasons underlying this failure are not yet defined, but different ESA administration protocols showed a significant reduction of such a large portion of patients (Hirsh 2007) suggesting the need of further protocol-optimization in managing NSCLC related anemia. Another disadvantage of the ESA treatments is that conflicting reports on the improvement in tumor response and survival were published. The use of ESAs in cancer is restricted by label on the settings of only cancer and only radiotherapy (Metanalisis Aapro 2012) (11 Meta-analyses 2010). This restriction implemented by the national authorities was based on the outcomes of the ENHANCE, DAHANCA-10, EPO-CAN-20 and AMG20010103 studies, in which found that ESA treatments increases cancer disease progression, thromboembolic events and mortality (Henke 2003 "ENHANCE", Overgaard 2007 "DAHANCA-10", Wright et al. J Clin Oncol 2007 "EPO-CAN-20" and Smith et al 2008 "AMG 20010103") (Metanalisis Aapro 2012).

Also reported was an increment of mortality in the ESA treated patients in the chemotherapy setting (Leyland-Jones 2005 "BEST"), (Hedenus 2003 "AMG 20000161"), (Thomas 2008) and "PREPARE" (Untch 2011a, 2011b), (IV: Katodritou 2008) (Bennett 2008, Glaspy 2010), but several studies contradicted the previous results reporting no significant difference in mortality (Piker et al 2008), (Moebus 2010) (Engert 2010), nor significant impact on the disease progression (Warner 2004, Reed 2005, Bohlius 2009, Gupta 2009, Ludwig 2009, Nagel 2011, Hershman 2009, Nitz 2011, Machtay 2007 and Glaspy et al 2010). There are also other studies that reported an increment of therapy effect by ESA treatment (Hadland 2009), and an increment of survival benefit as well (Littlewood 2001, Vansteenkiste 2002, and Delarue 2013).

These contradicting reports aimed to perform meta-analyses of the different trials. All meta-analyses reported that ESAs treatments reduce the transfusions requirements but still there are some contradicting findings regarding the mortality risk of ESA treatments in chemotherapy settings. (Bennett 2009, Bohlius 2009, Tonelli 2009, Hedenus 2005, Boogaerts 2006, Seidenfeld 2006, Ludwig 2009, Aapro 2009b, Glaspy 2010, Tonia et al Cochrane 2012). The reasons for such variability of conclusions might be due to differences in the study designs, heterogeneity of the treated patients, the varying ESA dose regimens and data analysis.

Since the first safety issues about ESA treatments were reported in 2003, several groups worked in the hypothesis of a functional EpoR in tumor context, as the logical mechanism exerting the tumor progression under ESA treatments in anemic cancer patients. In tumor tissue and carcinoma cell lines, EpoR mRNA expression levels were detected but very low in comparison with erythroid progenitors. The results were reproduced at protein level by western blot, immunohistochemistry, and in an animal model. These findings were however questioned by other groups due to the use of unspecific antibodies in some of the studies, the lack of signaling activation upon ESA stimulation, absence of EpoR in biopsies or the non-effect of ESAs treatment in tumor animal models. In the positive cases for specific EpoR expression at transcript and protein levels, EpoR levels were ranging from 10- up to 1000-fold lower than in Epo responsive cell lines, or by overexpression of receptor or in erythroid progenitors. This low level of EpoR expression in non-erythroid cells is an intrinsic liability of any experimental approach to study on EpoR presence and functionality upon ESA stimulations in tumor cells. Furthermore, the radioactive Epo-binding assay is one of the most sensitive approaches at the time of revealing ESA and EpoR binding behavior on the cellular surface. It has been reported that lower levels than 50 receptors per cell makes the measurements unreliable (Um 2007). The very low expression of EpoR in the tumor cell lines and tissue in addition to wide used of unspecific antibodies have constituted so far the "Achilles heel" of the functional studies of EpoR in a tumor context.

The characterization and prediction of an effective and safer ESA treatment of anemia in cancer and chemotherapy setting constitutes a complex question. The outcome is influenced by the dynamic interplay of many components, and it has to be addressed from multiple angles, which requires quantitative experimental studies at different levels. These different perspectives go from molecular studies of EpoR activation in a single cell to the study of ESAs pharmacokinetic (PK) and pharmacodynamics (PD) in carcinoma patients. Due to the complexity, non-linear relationship and involvement of multiple scales, this requires a Systems Biology approach that combines experimental data generation and mathematical modeling. The inventors focused in NSCLC, due to its high impact in the populations and the high prevalence of anemia. This would also simplify the heterogeneity of the outcomes in the ESA treatments and avoid any effect by the different underlying malignancies (11:24,32). Due to the wide variation of responses to ESA treatments in NSCLC patients, the inventors used individual patient data, in order to standardize and harmonize outcomes across the clinical trial. This approach will allow us to identify and correlate defined patient populations with hematological responses. The inventors also performed model-based predictions of the minimal personal effective ESA concentration (MPEC) in order to avoid the transient overdosing, which is suspected to be associated with thrombovascular events and potential EpoR activation in tumor context.

Mathematical modeling of biological systems has become a widely used approach to better understand the system behavior as a whole rather than observing isolated parts (Kitano, 2002). The rapid development of quantitative molecular biology (Cox and Mann, 2011) enables to calibrate mathematical models to experimental data and therefore to generate model predictions. Established approaches for modeling and parameter estimation are publicly available in software tools like SBML-PET, COPASI or PottersWheel (Zi and Klipp, 2006; Hoops et al., 2006; Maiwald and Timmer, 2008).

In view of the unsolved questions regarding the use of ESA in the treatment of anemia, in particular in the context of a cancer patient, it was an objective of the present invention to provide novel means and methods to assess the optimal dosage of ESA in a patient and thereby to avoid over- or under dosing. Furthermore the invention intends to provide diagnostic tools to supply the clinical practitioner with additional information about the anaemic status of a patient before preparing a treatment plan.

In one aspect the above problem is solved by a method for determining the dosage of an Erythropoiesis Stimulating Agent (ESA) that is sufficient for treating anemia in a patient, the method comprising the steps of (a) Calculating from the hemoglobin concentration of the patient from at least two separate time points the patient's individual hemoglobin degradation rate (degradation of hemoglobin per time), (b) Determining the concentration of hemoglobin from a recent blood sample obtained from the patient (the patient's present hemoglobin concentration), and (c) Calculating based on the patient's hemoglobin degradation rate and the patient's present hemoglobin concentration the ESA dosage sufficient for treating the anemia in the patient. The method is preferably performed in-vitro.

The step of calculating the ESA dosage is preferably performed using the non-linear dynamic pharmacokinetic (PK) hemoglobin (Hb) ESA-EPO-R pathway model as described in detail herein below.

In context of the herein described invention the hemoglobin concentration of the patient (or subject, terms which are used herein as synonyms) is preferably determined through blood samples taken from the patient. Methods for calculating the haemoglobin concentrations are well known in the art. Alternatively, since most anemia patients have a treatment history where haemoglobin concentrations were determined at multiple time points, the patients hemoglobin degradation rate may be calculated from these values taken from the individual patient's medical file.

Another aspect of the invention pertains to an ESA for use in the treatment of anemia of a patient, wherein the treatment comprises,
 (a) Calculating an ESA dosage according to a method of any of claims 1 to 3,
 (b) Administering to the patient an ESA dosage as calculated in (a),
 (c) Optionally, monitoring the patient's hemoglobin concentration over time after the administration in (b),
 (d) Optionally, repeating step (a) and (d).

The administration is preferably a subcutaneous injection.

The above problem is solved in a further aspect by an Erythropoiesis Stimulating Agent (ESA) for use in the personalized treatment of anemia, the treatment comprising the steps of
 (a) Administration of a (preferably clinically safe) dose of an ESA to an individual patient suffering from anemia,
 (b) Monitoring the clearance of said ESA from the serum in said patient,
 (c) Calculating from the clearance of said ESA in said patient the number of initial ESA binding sites present in said patient using a non-linear dynamic pharmacokinetic (PK) ESA-EPO-R pathway model, and
 (d) Adjusting the individual dosage of said ESA for said treatment in accordance with the number of ESA binding sites calculated in (c),
 (e) Optionally, repeating steps (b) to (d).

In an alternative aspect, the invention may relate to an Erythropoiesis Stimulating Agent (ESA) for use in the personalized treatment of anemia, the treatment comprising the steps of (a) Administration of a (preferably clinically safe dose) of an ESA to an individual patient suffering from anemia and determining the level of Hb at the time the ESA is administered, (b) Monitoring the concentration of Hb in said patient, (c) Calculating from change of concentration of Hb in said patient the number of initial ESA binding sites present in said patient using a non-linear dynamic pharmacokinetic (PK) hemoglobin (Hb) ESA-EPO-R pathway model, and (d) Adjusting the individual dosage of said ESA for said treatment in accordance with the number of ESA binding sites calculated in (c), (e) Optionally, repeating steps (b) to (d).

As an alternative embodiment the individual dosage of said ESA is calculated on the basis of the patient's hemoglobin degradation rate. Surprisingly it could be shown in context of the present invention that each patient has a specific hemoglobin degradation rate which correlates with the clinical development of anemia in the patient. Therefore the present invention discloses an ESA for the treatment of anemia in a patient wherein the ESA dosage using the herein described non-linear dynamic pharmacokinetic (PK) hemoglobin (Hb) ESA-EPO-R pathway model on basis of a predetermined hemoglobin degradation rate, the specific biding properties of the used ESA in the treatment (for example the $EC_{50}$ of EPOR occupancy by the ESA) and the present hemoglobin concentration at the time the treatment is started. Hence an embodiment pertains to an ESA for use in the treatment of anemia in a patient, wherein the treatment comprises the initial determination of the patient's hemoglobin degradation rate.

The hemoglobin degradation rate may either be determined by measuring hemoglobin concentrations in the patient at several time points, for example in an ESA naïve or ESA receiving patient, or using the patient's previous treatment history. In accordance with the herein described mathematical model the specific characteristics of the ESA to be used in therapy, for example CERA, are used for determining the ESA dosage.

Based in the initial experiments in vitro (ESA depletion experiments) as described in the example section, the mathematical model as disclosed describes the binding properties of each ESA: the association rate "$k_{on}$" and the dissociation rate "$k_{off}$" (the dissociation constant "$K_D$" is defined as koff/kon). Based in the binding properties of each ESA, the herein disclosed model can calculate the integral occupancy of the EpoR on human CFU-E for 60 minutes. The $EC_{50}$ (ESA concentration required to obtain half-maximum EpoR occupancy) is calculated for each ESA and this correlates with the ESA activity in hCFU-E. In the integrative non-linear dynamic pharmacokinetic (PK) hemoglobin (Hb) ESA-EPO-R pathway model, the integral occupancy of the ESA-EpoR is linked to Hb production. The amount of ESA-EpoR is, among all the other parameters, depending on the $k_{on}$ and the $k_{off}$ rate of the specific ESA. Based on the ESA depletion experiments, the mathematical model calculates $k_{on}$ and $k_{off}$ for each ESA. This data can be used (i) to calculate $EC_{50}$ values for each ESA and (ii) calculate Hb values based on ESA injections. Thereby, the using the non-linear dynamic pharmacokinetic (PK) hemoglobin (Hb) ESA-EPO-R pathway model of the invention, the ESA dosage for achieving a production of hemoglobin in the anemia patient that is sufficient to alleviate the anemia can be calculated.

The term "anemia" in context of the herein described invention shall refer to a condition wherein the red blood cells are reduced. Anemia is typically diagnosed on a complete blood count. Apart from reporting the number of red blood cells and the hemoglobin level, the automatic counters also measure the size of the red blood cells by flow cytometry, which is an important tool in distinguishing between the causes of anemia. Examination of a stained blood smear using a microscope can also be helpful, and it is sometimes a necessity in regions of the world where automated analysis is less accessible. In modern counters, four parameters (RBC count, hemoglobin concentration, MCV and RDW) are measured, allowing others (hematocrit, MCH and MCHC) to be calculated, and compared to values adjusted for age and sex. Some counters estimate hematocrit from direct measurements. In the context of the present invention anemia is present if an individual has a hemoglobin (Hb) concentration of less than 14 g/dL, more preferably of less than 12 g/dL, most preferably of less than 11 g/dL.

In certain embodiments of the invention the anemia to be treated in accordance with the described methods is an anemia that has developed according to any possible cause or disease. This includes all types of cancer, all inflammation-associated anemia (chronic infection disease, autoimmune or rheumatologic disorders and any other illnesses or treatments that results in anemia based on reduced endogenous Epo production, inefficient eryhtropoiesis or increased desruction of red blood cells). Furthermore, and particularly preferred, is that the anemia is caused by chronic kidney disease (CKD), myelodysplastic syndrome (MDS), or is anemia associated to myelofibrosis, anemia in context of HIV, aplastic anemias, anemia in premature infants, non-severe aplastic anemia, anemia in beta thalassemia, anemia in sickle cell disease and ESA erythropoiesis stimulation after allogeneic hematopoietic stem cell transplantation.

The inventors of the present invention surprisingly discovered that a mathematical model describing the EPO-EPO-R signaling pathway in a cell can be adapted to predict the behavior of not only ESAs in a cell, but also of the dynamics of ESAs administered to a patient. Initially the model is able to describe at cellular level the activity of the different ESAs based in the affinity of each ESA (time of EpoR occupancy). This activity corresponds to the EPO-R activation by ESA binding to the EPO receptor. This activation of the EPO-R will induce the proliferation and maturation of the erythropogenitors, the main cellular population on the body that express EpoR into erythrocytes. For the present invention the initial core model that describes the EpoR activation at cellular level by ESA was extended in order to be used in a physiological situation in an organism, in particular a human patient. Clearance of an administered ESA in the blood compartment, transport of an subcutaneous administered ESA into the blood compartment and saturable clearance of the ESA in the interstitial compartment were added to the initial model. This extended version of the initial ESA-EPO-R model was surprisingly able to describe the published pharmacokinetic (PK) and pharmacodynamics (PD) experimental data of each ESA as shown in the examples. The inventors could characterize induced anemia by cancer and chemotherapy in individual patients at colony forming unit of erythroids (CFU-E), the progenitors of the erythroids. It was observed that patients in the same cancer type and disease stage (FIG. 5c) show different numbers of CFU-E. This explains the different ESA treatment outcomes observed in patients—40% of the NSCLC patients do not respond to ESA treatment in the current approved posology (protocol to treat anemic patients with cancer). Lower levels of CFU-E means lower levels of response to ESA treatments and it correlated with the individual outcomes at hemoglobin levels (Hb).

In the context of the invention which is described in the following, the mathematical models are all based on the basic findings as published and publically accessible in the publication Becker V et al., Science. 2010 Jun. 11;328 (5984):1404-8. This reference is incorporated in its entirety, for the purpose of understanding the application of the mathematical models in the present invention. The models used in context of the present invention were adjusted to answer the respective questions of the herein disclosed invention. In this respect the term "non-linear dynamic EPO-EPO-R pathway model" shall refer to the model as published by the above Becker V et al. 2010 reference. The term "non-linear dynamic ESA-EPO-R pathway model" shall refer to an new version of the non-linear dynamic EPO-EPO-R pathway model, which describes the binding/dissociation dynamics of ESAs to the EPO-R on a cellular level. The term "non-linear dynamic pharmacokinetic ESA-EPO-R pathway model" shall refer to the non-linear dynamic ESA-EPO-R pathway model which is adjusted to the situation in an organism, in particular a human patient. The basic rationales for the models disclosed herein are provided in the Materials and Methods section of the present application.

Thus it is a preferred embodiment that the non-linear dynamic pharmacokinetic (PK) ESA-EPO-R pathway model considers clearance of the administered ESA in the blood compartment, transport of the administered ESA from the interstitial compartment into the blood compartment, and clearance of the ESA in the interstitial compartment.

The basic application of the mathematical methods as required by the herein described inventive methods is standard to the person of skill in the field of systems biology. Using the information as provided by the present patent application, the person of skill in view also of the Becker V et al. 2010 publication can perform the necessary steps to work the invention.

For the present disclosure the following variables, constants and acronyms are used:

TABLE 1

Acronyms

| | |
|---|---|
| CFU-E | Colony forming unit-erythroid |
| NSCLC | Non-small cell lung carcinoma |
| Hb | Hemoglobin |
| RBC | Red blood cells |
| Epo | Erythropoietin |
| EpoR | Erythropoietin receptor |
| PK | Pharmacokinetics |
| PD | Pharmacodynamics |
| MEPC | Minimal Personal Effective ESA Concentration |
| CKD | Chronic kidney disease |
| MDS | Myelodysplastic syndrome |
| NESP | Novel erythropoiesis stimulating protein |
| CERA | Continuous erythropoietin receptor activator |
| STAT5 | Signal transducer and activator of transcription 5 |
| EC50 | Half-maximal effective concentrations |
| ODE | Ordinary differential equation |
| U | Units |

TABLE 2

Variables

| | |
|---|---|
| ESA | Erythropoiesis-stimulating agent in medium/blood |
| Epo | Erythropoietin |
| EpoR | Erythropoietin receptor |
| ESAEpoR | Complex of ESA bound to EpoR on the cell surface |
| ESAEpoR$_i$ | Internalized complex of ESA bound to EpoR |
| dESA$_i$ | Intracellular degraded ESA |
| dESA$_e$ | Extracelullar degraded ESA |
| ESA$_{SC}$ | ESA in the subcutaneous compartment |
| Hb | Hemoglobin in blood |

TABLE 3

Kinetic constants

| | |
|---|---|
| $k_{sc\_clear}$ | ESA clearance constant in the subcutaneous compartment |
| $k_{sc\_clear\_sat}$ | Saturation of ESA clearance in subcutaneous compartment |
| $k_{sc\_out}$ | ESA transportation constant to the blood compartment |
| $k_{clear}$ | ESA clearance constant in the blood compartment |
| $k_{on}$ | ESA-EpoR association rate/on-rate |
| $k_{off}$ | ESA-EpoR dissociation rate/off-rate |
| $K_D$ | ESA-EpoR dissociation constant ($k_{off}/k_{on}$) |
| $k_t$ | Ligand-independent receptor turnover rate |
| $B_{max}$ | Number of ESA binding sites per cell/per patient |
| $k_e$ | ESA-EpoR complex internalization constant |
| $k_{ex}$ | ESA and EpoR recycling constant |
| $k_{di}$ | Intracellular ESA degradation constant |
| $k_{de}$ | Extracellular ESA degradation constant |
| $k_{Hb\_pro}$ | Hemoglobin production constant by the ESA-EpoR complex |
| $K_{Hb\_deg}$ | Hemoglobin degradation constant (net loss of hemoglobin) |

The models disclosed in the present application are based on the following ordinary differential equations with reference to FIG. 6. This model describes the following reaction scheme which is based on prior biological knowledge. The ESA binds reversibly ($k_{on}$ respectively $k_{off}$) to the Epo receptor (EPO-R) which is exposed on the cell surface. Thereby, the ESA-receptor complex gets activated and can induce phosphorylation of downstream signaling molecules like STAT5. The ESA-receptor complex is then internalized ($k_e$) into intracellular receptor pools where ESA is either exported ($k_{ex}$) or degraded ($k_{de}$ and $k_{di}$) and the receptor can translocate back to the membrane ($k_{ex}$). In addition, a ligand independent turnover ($k_t$) of EpoR ensures that the cell is sensitive for a broad range of ligand concentrations. In the equations [ ] denote concentrations of the respective components. These are, EpoR or EPO-R is the EPO receptor, ESAEpoR is the complex of ESA bound to the EPO-R. ESAEpoR$_i$ is the internalized complex. dESA is degraded ESA, either cell-internally (dESAi) or extracellular (dESAe). The equations are:

$$\frac{d[ESA]}{dt} = -k_{on} \cdot [ESA] \cdot [EpoR] + k_{off} \cdot [ESAEpoR] + k_{ex} \cdot [ESAEpoR_i] \quad (1.1)$$

$$\frac{d[EpoR]}{dt} = -k_{on} \cdot [ESA] \cdot [EpoR] + k_{off} \cdot [ESAEpoR] + k_t \cdot B_{max} - k_t \cdot [EpoR] + k_{ex} \cdot [ESAEpoR_i] \quad (1.2)$$

$$\frac{d[ESAEpoR]}{dt} = k_{on} \cdot [ESA] \cdot [EpoR] - k_{off} \cdot [ESAEpoR] - k_e \cdot [ESAEpoR] \quad (1.3)$$

$$\frac{d[ESAEpoR_i]}{dt} = k_e \cdot [ESAEpoR] - k_{ex} \cdot [ESAEpoR_i] - k_{di} \cdot [ESAEpoR_i] - k_{de} \cdot [ESAEpoR_i] \quad (1.4)$$

$$\frac{d[dESAi]}{dt} = k_{di} \cdot [ESAEpoR_i] \quad (1.5)$$

$$\frac{d[dESAe]}{dt} = k_{de} \cdot [ESAEpoR_i]. \quad (1.6)$$

For the model simulating the in-vivo patient situation this model is extended resulting in system of seven coupled ordinary differential equations (ODE). The expanded model in FIG. (6b) describes the situation including the blood and interstitium compartments. Intraveneous ESA is either cleared in the blood compartment ($k_{clear}$) or binds to the EPO-R ($k_{on}$, $k_{off}$). Subcutaneous applied ESA ($ESA_{SC}$) is transported to the blood compartment ($k_{sc\_out}$) or saturable cleared in the interstitial compartment ($k_{sc\_clear\_sat}$). The non-linear dynamic pharmacokinetic ESA-EPO-R pathway model:

$$\frac{d[ESA_{SC}]}{dt} = -k_{sc\_clear} \cdot \frac{[ESA_{SC}]}{(k_{sc\_clear\_sat} + [ESA_{SC}])} - k_{sc\_out} \cdot [ESA_{SC}] \quad (2.1.)$$

$$\frac{d[ESA]}{dt} = k_{sc_{out}} \cdot [ESA_{SC}] - k_{clear} \cdot [ESA] - k_{on} \cdot [ESA] \cdot [EpoR] + k_{off} \cdot [ESAEpoR] + k_{ex} \cdot [ESAEpoR_i] \quad (2.2.)$$

$$\frac{d[EpoR]}{dt} = -k_{on} \cdot [ESA] \cdot [EpoR] + k_{off} \cdot [ESAEpoR] + k_t \cdot B_{max} - k_t \cdot [EpoR] + k_{ex} \cdot [ESAEpoR_i] \quad (2.3.)$$

$$\frac{d[ESAEpoR]}{dt} = k_{on} \cdot [ESA] \cdot [EpoR] - k_{off} \cdot [ESAEpoR] - k_e \cdot [ESAEpoR] \quad (2.4.)$$

$$\frac{d[ESAEpoR_i]}{dt} = k_e \cdot [ESAEpoR] - k_{ex} \cdot [ESAEpoR_i] - k_{di} \cdot [ESAEpoR_i] - k_{de} \cdot [ESAEpoR_i] \quad (2.5.)$$

$$\frac{d[dESAi]}{dt} = k_{di} \cdot [ESAEpoR_i] \quad (2.6.)$$

$$\frac{d[dESAe]}{dt} = k_{de} \cdot [ESAEpoR_i]. \quad (2.7.)$$

Since the amount of hemoglobin (Hb) in a patients serum is directly correlated to the activity of ESA-EPO-R system, the invention may instead of determining the concentration of the ESA after initial administration of the ESA as a function of time, determine the Hb concentration, which is a standard parameter observed during anemia treatment. In this embodiment, the above model comprises the additional reactions of the production of Hb by the activated ESA-EPO-R ($k_{Hb\_pro}$) and the patient specific degradation of Hb ($k_{Hb\_deg}$).

In this case the model includes the additional ODE:

$$\frac{d[Hb]}{dt} = k_{Hb_{pro}} \cdot [ESAEpoR] - k_{Hb_{deg}} \cdot [Hb] \quad (2.8.)$$

For both models the dissociation constant of $K_D$ is defined as $$K_D = k_{off}/k_{on} \quad (3.1)$$

In these models $B_{max}$ is the initial number of binding sites for ESA.

Further explanation of the equations is provided in the example section and FIG. 6.

The values for the respective concentrations of elements and the all constants used in the above equations can be determined experimentally using, for example, a method known to the skilled person or the methods provided herein below in the example section.

The object of the present invention is solved in an additional aspect by an Erythropoiesis Stimulating Agent (ESA) for use in a method of diagnosing the anemic status in a patient, the method comprising the steps of (a) Administering to said patient a clinically safe dosis of an ESA, (b) Assessing the clearance of the administered ESA in the serum of said patient over time, (c) Calculating from the clearance of said ESA using a non-linear dynamic pharmacokinetic (PK) ESA-EPO-R pathway model the amount of ESA binding sites in said patient, which is predictive for the anemic status of the patient.

In accordance with the present invention, a clinically safe dose of an ESA is a dose approved by the authorities for the treatment of anemia.

In the herein described methods clearance rate of an ESA in the serum of a patient is determined. Preferably, and this holds true for all aspects and embodiments as described herein, the clearance rate (or change of concentration) of said ESA is determined based on the initial dose of ESA administered to a patient. Subsequent to the initial ESA administration, samples obtained from a patient can be analyzed for the remaining ESA concentration for at least one time point subsequent to the initial ESA treatment. Ideally, the ESA concentration is observed over several time points, for example 1 to 6 weeks, preferably 1 to 3 weeks, and includes at least 2, preferably 5, more preferably 7 to 10 independent measurements of ESA concentration at different time points. An example for an observation plan would be the administration of the ESA at day 0, and the subsequent measuring of the ESA concentration in the patient at days 1, 2, 3, 5, 7, 10 and 14. This may be adjusted depending on the clinical scenario. For the alternative embodiment of the invention regarding the calculation of initial ESA binding sites based on the observation of the change of Hb concentration in a patient, the same principle is applied.

In a certain embodiment of the invention the ESA is any ESA known to the skilled person, which includes in particular EPO biosimilars, but is preferably selected from the group of Epoetin alfa, Epoetin beta, Novel erythropoiesis stimulating protein (NESP) and Continuous erythropoietin receptor activator (CERA). CERA is preferred for the herein described invention.

The problem of the invention is also solved by a method for monitoring anemia in a patient who received at an earlier time point a dose of an ESA, comprising the steps of (a) Providing a serum sample from a patient suffering from anemia who received at an earlier time point a dose of an ESA, (b) Measuring the concentration of hemoglobin in said sample, (c) Calculating the amount of ESA binding sites based on the hemoglobin concentration in said sample using a non-linear dynamic pharmacokinetic (PK) ESA-EPO-R pathway model, wherein the amount of ESA binding sites indicates the anemic status of a patient.

Preferable the calculation is further based on the initial ESA dose, and the initial Hb concentration in the patient at the time the ESA was administered.

In context of the here described invention a patient is preferably a patient that is suffering from anemia in the context of a cancer disease, the cancer disease preferably being a lung cancer such as non-small cell lung cancer (NSCLC).

In preferred embodiments the non-linear dynamic pharmacokinetic (PK) ESA-EPO-R pathway model is based on a system of the ordinary differential equations (ODE) as described above. In this context the invention seeks to obtain the initial number of ESA binding sites, which is $B_{max}$. $B_{max}$ is therefore predictive for or an approximation of the colony forming unitserythroid (CFU-E).

Another aspect of the invention pertains to a method for identifying an Erythropoiesis Stimulating Agent (ESA) having a specific activity for cells with a high cell surface expression of Erythropoietin-receptor (EPO-R), comprising the steps of
 (a) Obtaining the half maximal effective concentrations (EC50) of a candidate ESA and a reference ESA for EPO-R activation in a first cell,
 (b) Obtaining the EPO-R activation induced by the candidate ESA and the reference ESA at their respective EC50 as obtained in (a) in a second cell, wherein said second cell is characterized by a significantly lower cell surface expression of EPO-R compared to the first cell,
wherein a decreased activation of EPO-R in said second cell by the candidate ESA compared to the activation of EPO-R in said second cell by the reference ESA, is indicative for the specificity of said candidate ESA for cells with a strong cell surface expression of EPO-R.

The above method may be performed solely in-silico or in-vitro. Preferably Epoetin alfa or beta are selected as reference ESA. However also other ESA which have similar characteristics, which can be derived from performing the inventive method, can be used as reference ESA.

Preferred is however that the method is an in-silico method and that said EPO-R activation is calculated with a non-linear dynamic ESA-EPO-R pathway model, more preferably according to the equations as described above. The EPO-R activation is preferable the integral of ESA bound to the EPO receptor ([ESAEPO-R]), for example for the first 60 minutes after stimulation. The time frame is however not essential to obtain the activation of the EPO signaling.

Preferably the calculation of the EPO-R activation in context of the above in-silico method comprises the input or the obtaining of the dissociation constant KD for at least the candidate ESA, and predicting the EPO-R activation over a period of time according to a non-linear dynamic ESA-EPO-R pathway model.

The ESA identified by the method is specific for cells expressing high amount of cell surface EPO-R and therefore, this ESA is characterized by being specific for colony forming unit-erythroid (CFU-E) cells. Cells having a low cell surface expression of EPO-R are in context of the present invention tumor cells, such as lung cancer tumor cells, in particular non-small cell lung cancer cells.

For performing the method in-vitro, it may be preferred that said first cell is a cell ectopically expressing EPO-R, such as H838-EpoR, and/or wherein said second cell is not ectopically expressing EPO-R, such as H838.

The problem of the invention is additionally solved by a computer implemented method for predicting or assessing the number of colony forming units-erythroid (CFU-E) or an approximation thereof, in a patient, wherein the patient has received an administration of an ESA at an earlier first point of time, the method comprising the steps of:
 (a) Obtaining the initial administered ESA dose,
 (b) Obtaining the concentration of said ESA in a serum sample of said patient at at least one second time point after the initial administration of said ESA to said patient.
 (c) Determining the concentration rate of said ESA as a function of time in said patient
 (d) Calculating based on a non-linear pharmacokinetic (PK) ESA-EPO-R model and the concentration rate of said ESA in said patient the initial number of ESA binding sites in said patient,
wherein the initial number of ESA binding sites in said patient is predictive for the number of CFU-E in said patient.

An alternative aspect provides a computer implemented method for predicting or assessing the number of colony forming unit-erythroid (CFU-E) or an approximation thereof, in a patient, wherein the patient has received an administration of an ESA at an earlier first point of time, the method comprising the steps of:
 (a) Obtaining the hemoglobin (Hb) concentration in said patient at the time point of the initial ESA administration,
 (b) Obtaining the concentration of Hb in said patient at at least one second time point after the initial administration of said ESA to said patient.
 (c) Determining the change in Hb in said patient as a function of time,
 (d) Calculating based on the change of Hb in said patient using a non-linear pharmacokinetic (PK) ESA-EPO-R model the initial number of ESA binding sites in said patient,
wherein the initial number of ESA binding sites in said patient is predictive for the number of CFU-E in said patient.

Another aspect of the invention then relates to a computer implemented method for predicting the amount of initial ESA binding sites in a patient, the method comprising the steps of: obtaining the clearance rate of an ESA after initial administration of said ESA to a patient as a function of serum concentration of the ESA of time, calculating based on a non-linear pathway model the number of initial ESA binding sites (Bmax). Preferably the non-linear pathway model is a non-linear dynamic PK ESA-EPO-R pathway model.

The computer implemented method for assessing the number of ESA binding sites in a cell, or a an organism, may alternatively comprise the steps of
 (a) In vitro determination of the clearance rate of an ESA in said cell or organism at at least one time point subsequent to the addition/administration of an initial ESA dose to said cell or organism,
 (b) Calculating the amount of ESA binding sites in said cell or organism based on the clearance rate of the ESA using a non-linear dynamic EPO-R pathway model.

However, preferred is the above method wherein said organism is a patient, preferably a human patient, or wherein said cell is a cell endogenously expressing the EPO-R receptor, such as a red blood cell precursor cell, or a tumor cell.

Preferably said organism is a human patient. In this scenario step (a) constitutes the in vitro determination of the clearance rate of an ESA in a serum sample of a patient at a time point subsequent to the administration of an initial ESA dose to said patient, and step (b) constitutes calculating the amount of ESA binding sites based on the clearance rate of the ESA using a non-linear dynamic EPO-R pathway model.

In a preferred embodiment of the invention the computer implemented method requires for the calculating step (b) as input the clearance rate of an ESA in said cell or organism as a function of ESA concentration over time as determined in (a), and a dissociation constant $K_D$ that is specific for the ESA added/administered to said cell or organism.

Yet another aspect of the invention provides a computer-readable storage medium having computer-executable instructions stored, that, when executed, cause a computer to perform a computer implemented method according to the present invention.

In preferred embodiments of all aspects of the invention the $K_D$ of the ESA is about 16 pM for Epoetin alfa, about 17 pM for Epoetin beta, about 789 pM for NESP and about 982 pM for CERA.

In a further aspect of the present invention there is provided an Erythropoiesis Stimulating Agent (ESA) for use in the treatment of anemia, the treatment comprising the steps of
(a) Obtaining the level of hemoglobin in a patient suffering from anemia,
(b) Calculating from the level of hemoglobin (Hb) in said patient the number of initial ESA binding sites present in said patient using a non-linear dynamic Hb ESA-EPO-R pathway model, and
(c) Determining a therapeutically effective dosage of an ESA for use in a treatment of anemia in said patient based on the number of initial ESA binding sites in said patient as calculated in (b).

The non-linear dynamic Hb ESA-EPO-R pathway model used in this aspect takes into account the additional reactions of the production of Hb based on the active ESA-EPO-R complex and a patients individual Hb degradation.

The term "treatment" as used herein covers any treatment of a disease or condition (e. g., anemia) in a mammal, particularly a human, and includes: (i) preventing the disease or condition from occurring in a subject which may be predisposed to the disease but has not yet been diagnosed as having it; (ii) inhibiting the disease or condition, i. e. arresting its development; or (iii) relieving the disease or condition, i. e. causing its regression or the amelioration of its symptoms.

As used herein, the term "therapeutically effective amount" refers to that amount of a polymer-modified synthetic erythropoiesis stimulating protein which, when administered to a mammal in need thereof, is sufficient to effect treatment (as defined above), for example, as inducer of red cell production, an anti-anemia agent, etc. The amount that constitutes a "therapeutically effective amount" will vary depending on the ESA, the condition or disease and its severity, and the patient to be treated, its weight, age, gender, etc., but may be determined routinely by one of ordinary skill in the art with regard to contemporary knowledge and to this disclosure.

Administration of the ESA of the invention may be performed via any accepted systemic or local route known for the respective ESA, for example, via parenteral, oral (particularly for infant formulations), intravenous, nasal, bronchial inhalation (i. e., aerosol formulation), transdermal or topical routes, in the form of solid, semi-solid or liquid or aerosol dosage forms, such as, for example, tablets, pills, capsules, powders, liquids, solutions, emulsion, injectables, suspensions, suppositories, aerosols or the like. The erythropoiesis stimulating agents of the invention can also be administered in sustained or controlled release dosage forms, including depot injections, osmotic pumps, pills, transdermal (including electrotransport) patches, and the like, for the prolonged administration of the polypeptide at a predetermined rate, preferably in unit dosage forms suitable for single administration of precise dosages. The compositions will include a conventional pharmaceutical carrier or excipient and a protein antagonist or agonist of the invention and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

The inventors furthermore discovered the mathematical model of the invention can be used to determine the biological activity of an ESA candidate compound. Hence there is also provided a method for estimating the biological activity of an ESA, comprising the steps of:
(a) Calculating the occupancy of the EPO receptor on human CFU-E cells in re-sponse to a range of ESA concentrations using the non-linear dynamic phar-macokinetic (PK) ESA-EPO-R pathway model,
(b) Calculating the area under the curve for the ESA from the resultant of step (a) as a measure for EPO receptor occupancy of the ESA,
(c) Calculating the concentration of the ESA for which the half maximum occupancy of the EPO receptor is reached to obtain an EC50ESA,
(d) Compare the EC50ESA with a predetermined EC50EPOalfa or EC50EPOalfa, Wherein the difference between the EC50ESA compared to the predetermined EC50EPOalfa or EC50EPOalfa correlates with the difference of the biological activity of the ESA when compared with the biological activity of EPO alfa or EPO beta.

The biological activity of the ESA or EPO is preferably provided in Units (U) per µg and described the ability of the ESA to induce blood cell proliferation.

The EC50EPOalfa or EC50EPOalfa may be predetermined by performing in addition steps (a) to (c) of the aforementioned method using EPO alfa or EPO beta as "ESA" to obtain in step (c) the values for EC50EPOalfa or EC50EPOalfa. The biological activity of EPO alfa or EPO beta is well known. Alternatively, other ESAs for which the biological activity is known may be used as a reference.

In this aspect the non-linear dynamic pharmacokinetic (PK) ESA-EPO-R pathway model as described herein is used.

Another aspect of the invention further An Erythropoiesis Stimulating Agent (ESA) for use in the treatment of anemia in a subject, the treatment comprising the steps of
(a) Determining or providing hemoglobin concentrations in the subject from at least two separate time points and calculating therefrom a subject specific he-moglobin degradation rate,
(b) Determining the present hemoglobin concentration in the subject,
(c) Calculating from the subject specific hemoglobin degradation rate and the hemoglobin concentration in the subject the dosage of an ESA sufficient to treat the anemia in the subject using a non-linear dynamic pharmacokinetic (PK) hemoglobin (Hb) ESA-EPO-R pathway model, and (d) Administering to the subject the calculated dosage of the ESA as determined in (c), (e) Optionally, monitoring the hemoglobin concentration in the subject after administration of the ESA and adjusting the next dosage of the ESA by repeating steps (b) to (d).

The invention also pertains to a computer implemented method for determining an ESA dosage for an anemia treatment in a subject, the method comprising the steps of (a) providing at least two separate hemoglobin concentrations of the subject before the treatment, (b) calculating from the hemoglobin concentrations in (a) a subject specific hemoglobin degradation rate, (c) calculating from the subject specific hemoglobin degradation rate as deter-mined in (b) and from a present hemoglobin concentration in the patient, an ESA dosage using a non-linear dynamic pharmacokinetic (PK) hemoglobin (Hb) ESA-EPO-R pathway model.

The method may further comprise repeating step (c) for obtaining an adjusted next ESA dosage.

Finally there is provided a method for the stratification of an anemia patient receiving ESA treatment, the method comprising the determination of a patient specific hemoglobin degradation rate by monitoring hemoglobin concentration in the patient over time and calculating therefrom the patient specific hemoglobin degradation rate and, wherein an increased hemoglobin degradation rate in the patient compared to a reference value indicates a decreased response to the ESA treatment, and wherein an increased hemoglobin deg-radation rate in the patient compared to a reference value indicates that the patient is overdosed.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: Characterization of ESA binding properties based on the determination of ligand depletion and the ESA-EpoR mathematical model. (a) Parental BaF3 cells (BaF3) and BaF3 stably expressing the murine EpoR (BaF3-mEpoR) were incubated with 100 pM Epo alfa or 100 pM Epo beta. At the indicated times the supernatant was removed and the concentration of Epo was quantified by an ELISA assay. Based on this data the association rate $k_{on}$, the dissociation rate $k_{off}$ and the number of ESA binding sides at the cellular surface ($B_{max}$) were estimated by the ESA-EpoR mathematical model and the ESA-specific dissociation constant $K_D$ ($k_{off}/k_{on}$) was calculated. (b) BaF3 cells and BaF3 stably expressing the human EpoR (BaF3-hEpoR) were incubated with Epo alfa, Epo beta, NESP and CERA. At the indicated times the supernatant was removed and the concentration of Epo was quantified by an ELISA assay. Based on this data the association rate $k_{on}$, the dissociation rate $k_{off}$ and the number of ESA binding sides at the cellular surface ($B_{max}$) were estimated by the ESA-EpoR mathematical model and the ESA-specific dissociation constant $K_D$ ($k_{off}/k_{on}$) was calculated. (c) Predicted by the ESA-EpoR mathematical model for each ESA the association rate $k_{on}$ was plotted against the dissociation rate $k_{off}$. The calculated ESA-specific dissociation constant $K_D$ for the hEpoR is indicated by symbols. Shaded areas around the symbols indicate the confidence interval of the $K_D$ ($k_{off}/k_{on}$). The heatmap displays the values of the $K_{ID}$.

FIG. 2: Presence of a functional EpoR on human lung cancer cell lines. (a) Total mRNA was extracted from the NSCLC cell lines H838, H1299, A549 and H1944 and the expression of the EpoR mRNA was determined by qRT-PCR. The EpoR mRNA expression in H838 cells was used as reference. (b) BaF3 cells and BaF3-hEpoR as well as the indicated NSCLC cell lines were stimulated with 10 U/ml of Epo beta for 10 min or were left untreated and were lysed. The abundance of the phosphorylated EpoR (pEpoR) and the total EpoR was determined by immunoprecipitation (IP) and quantitative immunoblotting (IB). The experiment was performed in biological triplicates and one representative immunoblot is shown. (c) The NSCLC cell lines H838, H1299, A549 and H1944 were stimulated with 4 pM of Epo beta and the Epo depletion kinetics was determined by an ELISA assay up to 8000 min incubation time. The ESA-EpoR mathematical model was employed to describe the depletion kinetics in all analyzed NSCLC cell lines and to determine the number of ESA binding sites/cell ($B_{max}$).

FIG. 3: H838-EpoR cells can serve as a model for human CFU-E cells concerning EpoR levels (a) Human hematopoietic stem cells (hHSC) from cord blood were isolated and differentiated to human CFU-E (hCFU-E) as described. hCFU-E and hHSC cells that served as negative control (a) as well as NSCLC cell line H838 stably transduced with hEpoR (H838-EpoR) (b) were stimulated with 4 pM of Epo beta and time-resolved analysis of the depletion kinetics was monitored via ELISA assay over the time period of 200 min (experimental data—dots). The model could describe the depletion kinetics (model—solid line) and estimate KD and Bmax values. (c) Quantitative immunoblot demonstrating overexpression level of human EpoR in H838-hEpoR cells compared to parental H838. Functionality of EpoR is shown by Epo-induced phosphorylation of receptor and JAK2.

FIG. 4: CERA preferentially activates cells with high EpoR expression (a) Model based prediction of differential dose response for EpoR activation in H838-hEpoR by different ESAS (left panel). Blue and red lines correspond to Epo beta and CERA respectively. Dashed lines indicated the EC50 of each ESA in the activation of the erythroprogenitors, 141 pM and 1048 pM for Epo beta and CERA respectively. Right panel represents the validation of the model prediction. Epo beta and CERA activates EpoR in a very different range of concentrations. H838-hEpoR cells were stimulated during 10 minutes with increasing concentrations of each ESA. Cells were lysated, EpoR immunoprecipitated and blotted against total and phosphorylated form. Blue circles represent experimental data upon Epo beta stimulation. Red circles represent experimental data corresponding to CERA stimulation. Solid lines are the activation trajectories predicted by the model. (B) Left panel represents the model based prediction of the integral EpoR activation by each EC50 during 60 minutes. Area under the curve shows no significant difference between Epo beta and CERA activation in H838-EpoR, Right panel shows the model based prediction of the integral EpoR activation by each EC50 during 60 minutes in H838. In this case the area under the curve indicates a probable lower activation of EpoR by CERA in comparison with Epo beta.

FIG. 5: Differential pharmacokinetic behavior of CERA among healthy and NSCLC subjects. (a) Pharmacokinetic behavior of increasing CERA concentrations in healthy volunteers. Colored circles are the mean values of CERA concentrations in serum, determined by ELISA assay. Solid lines represent the trajectories predicted of the CERA clearance for the given concentrations and the experimental data. (B) Pharmacokinetic behavior of increasing CERA concentrations in NSCLC patients in stage III or IV. Colored circles are the mean values of CERA concentrations in serum, determined by ELISA assay. Solid lines represent the trajectories predicted of the CERA clearance for the given concentrations and the experimental data. The different trajectories reported by the model, describes the experimental data and showed a reduction of 72%±16% in the CERA clearance capability of NSCLC patients. (c) Characterization and relative comparison of CERA clearance capability (% of CFU-E) of NSCLC patients and healthy subjects. The dashed line is the 100% clearance capability of CERA, which represents the normal capability of CERA clearance in healthy subjects. The pinky bars represent the number of NSCLC patients with a define % of CERA clearance capability compared to healthy subjects (individual PK data extracted from Hirsch et al 2007 clinical trial). The plot represents a general reduction of CFU-E population (% of CERA clearance capability) in NSCLC patients in comparison in comparison of the mean value in healthy subjects represented as 100%. It can be also notice different grades of reduction in the CFU-E population of NSCLC patients.

FIG. 6: Graphical representation of the basic and pharmacokinetic/pharmacodynamic mathematical model. (a) the reactions 1 to 6 are 1: Binding/unbinding of ESA to the Epo receptor (EpoR). The kon/koff rate constants of the binding/unbinding reaction are ESA specific and can be fully characterized using the trafficking model and the respective depletion data. 2: ESA-EpoR complex internalization. 3: Recycling to the cell membrane and dissociation of the internalized ESA-EpoR complex. 4: Production/degradation of EpoR at the cell membrane. The production/degradation reactions are in equilibrium defining a certain, cell type (a)/patient (b) specific amount of receptors at the cell surface characterized by Bmax parameter. 5: Degradation of internalized ESA-EpoR complex. 6: Degradation and release of internalized ESA-EpoR complex; (b) additional reactions 7 to 9 are 7: Clearance in the blood compartment, 8: Transport into blood compartment, 9: Saturable clearance in the interstitial compartment. (c) Calculation of $B_{max}$ based on the Hb levels further includes the reactions 10: Production of Hb triggered by the activated receptor complex, and 11: depletion of Hb in the blood of an individual.

Figure 7:
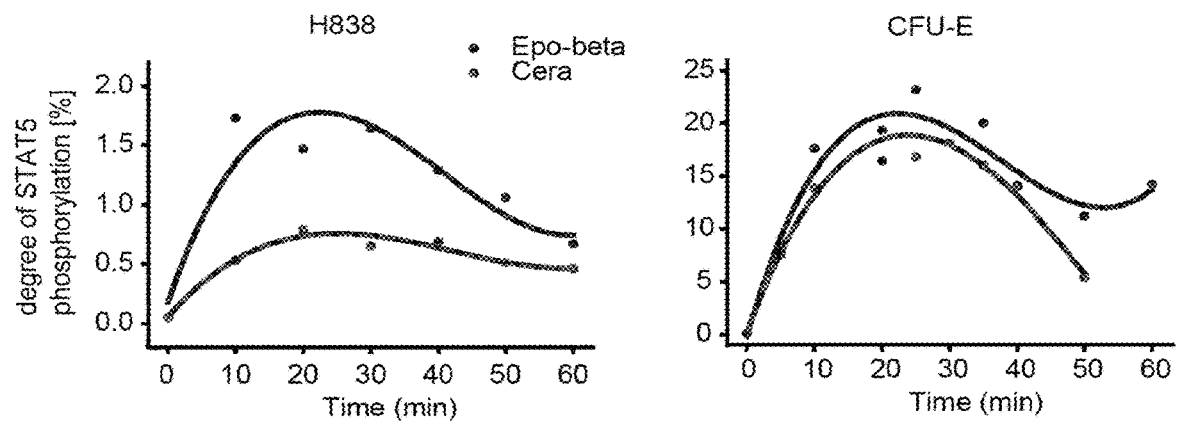

FIG. 7: CERA preferentially activates signal transduction in cells with high EpoR abundance. Quantification of STAT5 phosphorylation in H838 and hCFU-E cells upon Epo beta and CERA stimulation. H838 (left panel) and hCFU-E (right panel) cells were stimulated with 1331 pM of Epo beta and 8841 pM of CERA corresponding to the half-maximal activation of STAT5 phosphorylation in CFU-Es. Measurements of the degree of phosphorylated STAT5 (symbols) were performed by mass spectrometry. Solid lines indicate smoothing spline approximations.

FIG. 8: Individualized pharmacokinetics and pharmacodynamics in healthy subjects and NSCLC IIIB-IV patients treated with CERA. (a) Graphical representation of the equations (1 ... 11) of the integrative (PK/PD) ESA-EpoR mathematical model using the cell designer formalism. Hb: hemoglobin, sc: subcutaneous, dESAi: intracellular degraded ESA; dESAe: extracellular degraded ESA. (b) The pharmacokinetics and pharmacodynamics of the NSCLC patient (ID:2101, CSR NA17101 clinical trial) is shown in purple. The amount and timing of the CERA dose given to this patient is displayed in the top panel. In the middle panel, the pharmacokinetics of CERA is indicated. The concentration of CERA in the blood stream of this patient at different time points is symbolized by dots and the trajectories of the mathematical model are indicated by a solid line. In the lower panel the pharmacodynamics of hemoglobin (Hb) is shown indicating the experimental measurements by dots and model trajectories by a solid line. The model predicted ESA binding sites per patient and the Hb degradation rate are indicated. (c) The pharmacokinetics and pharmacodynamics of the healthy subject (ID:25, WP16422 clinical trial) is shown in green. The amount and timing of the CERA dose given to this individual is shown in the top panel. In the middle panel the pharmacokinetics of CERA displayed. The CERA concentration in the blood stream is indicated by dots and the solid line represents the model trajectory. The pharmacodynamics of hemoglobin (Hb) is shown in the lower panel. Dots correspond to experimental data and the solid line represents the model trajectory. The model predicted ESA binding sites/patient and the Hb degradation rate is indicated. (d) The distribution of ESA binding sites per patient and of the hemoglobin degradation rate in healthy subjects and NSCLC patients. The distribution of the Hb degradation rate (left panel) and of the ESA binding sites (Bmax) (right panel) in 88 healthy subjects (green) and 88 NSCLC patients (purple) is depicted.

FIG. 9: NSCLC patient stratification and individualized treatment recommendation by the integrative PK/PD ESA-EpoR mathematical model. (a) CERA treatment simulations according to the patient-specific parameters in three patients of the CSR NA17101 clinical trial. Patient 1, 2 and 3 correspond to ID2303, ID1022 and ID2652 respectively. Upper panels represent the CERA dose and regimens given to patients based on the current posology for NESP. Lower panels represent the outcome for the three patients. Dashed lines correspond to the optimal outcome that can be achieved within the limits of the current label for ESAs. Solid line represents the outcome for each patient predicted by the integrative PK/PD ESA-EpoR mathematical model. Shading represents the confidence interval of the model prediction for Hb levels. (b) Patient stratification based on the current ESA posology. The patient-specific ESA binding sites per patient and the Hb degradation rates estimated by the integrative PK/PD ESA-EpoR mathematical model for all patients in the CSR NA17101 clinical trial are indicated by the symbols. Patient 1, 2 and 3 studied in (a) are marked with black circles. Overdosed patients are defined by a Hb increment >2 g/dl in four weeks and/or reaching Hb levels >13 g/dl and Non-treatable patients are characterized by no increment of Hb levels during the treatment. (c) Model-based optimized ESA treatment of patient 1, 2 and 3. The upper panel represents the dose and regimens that the model recommends for each patient. The lower panel represents the model predicted treatment outcome for each patient. Dashed line corresponds to the ideal outcome based on the current label for ESAs. Solid line represents the outcome prediction by the model. Shading represents the assumed confidence interval of the Hb measurement. (d) Stratification of the 88 NSCLC IIIB-IV patients from the CSR NA17101 clinical trial. Patient 1, 2 and 3 are marked with a black circle. The lines indicate the maximal CERA doses required to successfully treat the respective patients at an interval of three weeks, except for patients with a very high Hb degradation rate and a high number of ESA binding sites that require weekly CERA doses.

EXAMPLES

Materials and Methods

Plasmids and Reagents.

Retroviral expression vectors were pMOWS-puro (Ketteler et al., 2002). The generation of hemagglutinin (HA)-tagged murine Epo receptor (pMOWS-HA-mEpoR) and of HA-tagged human EpoR (pMOWS-HA-hEpoR) was performed as described previously (Becker et al., 2010). Cells were either treated with Epo alfa (Cilag-Jansen), Epo beta (Roche), NESP (Amgen), or CERA (Roche) at indicated concentrations.

Cell Culture and Transfection.

Human lung adenocarcenoma cell lines A549, H838, H1299, H1944, H1650, H1975 and H2030 were purchased by ATCC and cultivated in Dulbecco's modified Eagle's Medium (DMEM, Lonza) supplemented with 10% fetal calf serum (FCS, Gibco) and 1% penicillin/streptomycin (Invitrogen). The Phoenix eco and Phoenix ampho packaging cell lines (Kinsella & Nolan, 1996) were cultured in DMEM (Gibco) supplemented with 10% FCS and 1% penicillin/streptomycin. BaF3 cells (Palacios & Steinmetz, 1985) were cultured in RPMI1640 (Invitrogen) including 10% FCS and supplemented with 10% WEHI conditioned medium as a source of IL-3. For the EpoR overexpressing cell lines H838 (H838-hEpoR) and BaF3 (BaF3-mEpoR and BaF3-hEpoR) 1.5 µg/ml puromycin (Sigma) was added to the respective medium.

To obtain hCFU-E cells, CD34+ cells were sorted by MACS (CD34-Multisort Kit, Miltenyi) from umbilical cord blood of healthy donors after written consent. CD34+ cells were expanded using Stem Span SFEM II supplemented with Stem Span CC110 (both StemCell Technology). After seven days of expansion cells were either washed extensively using IDMEM (Gibco) to remove cytokines and to initiate differentiation or cells were used for depletion experiments. For differentiation cells were cultivated in Stem Span SFEM II supplemented with 10 ng/ml IL-3 (R&D Systems), 50 ng/ml SCF (R&D Systems) and 6 U/ml Epo alpha (Cilag-Jansen) as published by Miharada 2006. After 4 days of cultivation in this media hCFU-E were harvested to perform depletion experiments. All cells were cultured at 37° C. with 5% CO2 incubation.

Transfection of Phoenix eco and Phoenix ampho cells was performed by calcium phosphate precipitation. Transducing supernatants were generated 24 h after transfection by passing through a 0.45 µm filter and supplemented with 8 µg/ml polybrene (Sigma). Stably transduced BaF3 cells expressing HA-tagged murine EpoR (BaF3-mEpoR cells) or HA-tagged human EpoR (BaF3-hEpoR cells) or H838 cells expressing HA-tagged human EpoR (H838-hEpoR cells) were selected in the presence of 1.5 µg/ml puromycin (Sigma) 48 h after transduction. Surface expression of EpoR in BaF3 and H838-hEpoR cells was verified by Flow cytometry analysis.

Flow Cytometry.

EpoR surface expression was verified by flow cytometry. Therefore H838-hEpoR cells were gently detached with Cell Dissociation Solution (Sigma) according to the manufacturer's instructions. BaF3-EpoR and H838-hEpoR cells were stained with anti-HA antibody (Roche) diluted 1:40 in 0.3% PBS/BSA for 20 min at 4° C. Followed by washing of cells with 0.3% PBS/BSA and incubation of secondary Cy5-labeled antibody against rat (Jackson Immuno Research), diluted 1:100 in 0.3% PBS/BSA, for 20 min at 4° C. in the dark. After washing samples with 0.3% PBS/BSA, propidium iodide (BD Biosciences) was added to exclude dead cells. Canto II (BD Bioscience) was used for sample analysis.

Depletion Experiments and ELISA

ESA depletion experiments were conducted in NSCLC tumor cell lines, BaF3, BaF3-mEpoR, BaF3-hEpoR, hCFU-E, hHSC cells. Tumor cells were seeded in 6 well-plates (TPP 92006) at a cellular concentration of 4×105 cells in 3 ml of proliferating media (DMEM supplemented with 10% FCS and 1%). Cells were kept at 37° C., 95% H2O and 5% CO2 during three days. On the third day cells were washed with DMEM (1% penicillin/streptomycin and 1 mg/ml BSA) and left them starving in 1 ml of washing media during 12 hours. Cells were stimulated with Epo alfa/beta within the indicated times and concentrations of the depletion plots. After the incubation time, media was recovered and kept at −80° C. till the conclusion of the experiment, cells were trypsinized and counted by hemoytometer chamber. Once the experiment was concluded ESAs concentration was measured by ELISA (Quantikine IVD ELISA Kit, R&D DEP00).

The experimental setting for the depletion measurements was different in the suspension cells; BaF3-hEpoR, BaF3-mEpoR, BaF3, hCFU-E and hHSC. In the transduced BaF3 cells, the experiments were conducted in between 9-14 days of selection with puromicin (1.5 µg/ml). Cells were washed three times in RPMI by centrifugation 5 minutes at 212×g, and starved 3 hours in RPMI (1% penicillin/streptomycin and BSA 1 mg/ml) at a concentration of 1×106 cells/ml. After the starvation period cells were adjusted to a final concentration of 40×106 cells/ml in 350 µl at 37° C. and 900 rpm in a Thermomixer compact of Eppendorf. Cells were stimulated by ESA during the indicated times in the plot and centrifuged during 5 minutes, at 4° C. and 2500 rpm. Supernatant was removed and kept at −80° C. ESAs measurements were performed by ELISA (Quantikine IVD ELISA Kit, R&D DEP00). ESAs depletion measurements were conducted in the same way in hCFU-E and hHSC with the only difference of the cell concentration 30×106 cells/ml, and the used media (Stem Span SFEM II).

Immunoprecipitation and Quantitative Immunoblotting.

For analysis of phosphorylated and total proteins human lung adenocarcenoma cell lines as well as H838-hEpoR cell line were seeded, cultivated for 72 h, starved for 3 h in DMEM with 1% penicillin/streptomycin, 2 mM L-glutamine (Gibco) and 1 mg/ml BSA and then stimulated with Epo beta or CERA at indicated concentrations for 10 min. Prior to experiments BaF3 cells were washed and resuspended in serum-depleted RPMI-1640 supplemented with 1% penicillin/streptomycin and 1 mg/ml BSA and starved for 3 h. Afterwards the cells were harvested and aliquoted in a density of 20×106/ml and stimulated with Epo beta at indicated concentrations for 10 min.

The cells were lysed with 1.25×NP-40 lysis buffer (1.25% NP-40, 187.5 mM NaCl, 25 mM Tris pH 7.4, 12.5 mM NaF, 1.25 mM EDTA pH 8.0, 1.25 mM ZnCl2 pH 4.0, 1.25 mM MgCl2, 1.25 mM Na3VO4, 12.5% glycerol supplemented with aprotinin and AEBSF). The protein concentrations in lysates were measured using the colorimetric BCA protein assay kit (Pierce Protein Research Products). For Immunoprecipitation analysis the lysates (1500-2000 µg protein for lung adenocarcenoma cell lines, 400 µg protein for BaF3 cells) were supplemented with antibodies to EpoR (R&D, MAB 307), JAK2 (Upstate) or STAT5A/B (Santa Cruz, C17) and Protein A sepharose (GE Healthcare) and rotated over night by 4° C. Immunoprecipitated proteins were separated by 10% SDS-PAGE and transferred to nitrocellulose membrane (0.2 μm pore, Schleicher & Schuell). For quantification purposes randomized non-chronological gel loading was performed (Schilling et al., 2005). For the detection of the phosphorylated proteins the blots were probed with mAbs specific for phosphotyrosine (pTyr) (Upstate, clone 4G10) and then with secondary horseradish peroxidase-coupled anti-mouse antibodies (Dianova). To remove antibodies, membranes were treated as described previously (Klingmüller et al., 1995) and subsequently incubated with pAbs for EpoR (Santa Cruz, C-20) and horseradish peroxidase-coupled anti-rabbit antibodies (Dianova). Detection was performed using ECL substrate (GE Healthcare). Immunoblot data were acquired with the CCD camera-based ImageQuant LAS 4000 (GE Healthcare) and quantification was performed with the ImageQuant TL version 7.0 software (GE Healthcare).

mRNA Isolation, cDNA Preparation and qPCR

For analysis of EpoR expression the cells were lysed and RNA extraction was performed using RNeasy Mini kit (Qiagen) according to the supplier's protocol. To obtain cDNA from RNA, the high-capacity cDNA reverse transcription kit (Applied Biosystems) was used according to manufacturer's instructions. Quantitative real-time PCR (qRT-PCR) analysis was performed using LightCycler 480 (Roche applied-Science). Samples were prepared with reagents of the LightCycler480 Probes Master Kit from Roche applied-Science. Specific primers were obtained from Eurofins MWG and universal probes (UPL) for TaqMan quantification of DNA from Roche applied-Science. Concentrations were normalized using the geometric mean of β-glucuronidase (GUSB) and esterase D (ESD). Primers targeting human EpoR: forward—ttggaggacttggtgtgtttc; reverse—agcttccatggctcatcct; ESD: forward—ttagatggacagttactccctgataa; reverse—ggttgcaatgaagtagtagctatgat; GUSB: forward—cgccctgcctatctgtattc; reverse—tccccacagggagtgtgtag.

Mass Spectrometry Analysis.

Cellular lysate were subjected to IP with a combination of two STAT5 antibodies, sc-1081 and sc-836 from Santa Cruz Biotechnology. Two IPs were pooled per lane. Proteins were separated by a 10% SDS-PAGE (GE Healthcare) in 1× Laemmli buffer (Laemmli 1970). Following coomassie staining with SimplyBlue™ SafeStain (Invitrogen) STAT5 gel bands were excised at approximately 90 kDa and cut into small pieces (1 mm3). Gel pieces were destained, reduced with DTT (dithiothreitol, SIGMA), alkylated with IAA (iodoacetamide, SIGMA) and digested with 0.3 μg trypsin in 100 mM NH4HCO3/5% acetonitrile buffer overnight. In-house produced one-source peptide/phosphopeptide ratio standards for STAT5A and STAT5B were added to the digests (Boehm 2014). Following a four-step peptide extraction performed sequentially with 100 mM NH4HCO3/5% acetonitrile, acetonitrile, 5% formic acid, and acetonitrile, the samples were concentrated in a speedvac (Eppendorf) and desalted with C18 Ziptips (Millipore) using solutions based on water, acetonitrile and formic acid. Samples were analyzed by EASY-nLC 1000 (Thermo Scientific) coupled to a Q Exactive™ Hybrid Quadrupole-Orbitrap Mass Spectrometer (Thermo Scientific). As precolumn we used Acclaim PepMap 100, 75 μm×2 cm, as analytical column we used Acclaim PepMap RSLC C18, 2 μm, 100 Å, 75 μm×25 cm. Survey full scan MS spectra were acquired at resolution R=70,000 and analyzed for the native and labelled STAT5 peptide and phosphopeptide pairs with Xcalibur 3.0.63 (Thermo).

The in vitro trafficking model (FIG. 6a) was extended to a pharmaco-kinetic/pharmacodynamics (PK/PD) model (FIG. 6b) by including blood and interstitium compartments and patient specific PK data obtained by either intravenous (IV) or subcutaneous (SC) injections of ESA/CERA. Additionally, the model provides the link between ESA bound to the EpoR (ESA_EpoR) and haemoglobin levels (Hb) measured in patients. The model consists of the following additional reactions:

7. Clearance in the blood compartment.
8. Transport into blood compartment.
9. Saturable clearance in the interstitial compartment.
10. Production of Hb triggered by the activated receptor complex.
11. Patient specific degradation of Hb.

The reaction rate equations are given by:
1. "$k_{on}$*ESA*EpoR" and "$k_{off}$*ESA_EpoR"
2. "$k_e$*ESA_EpoR"
3. "$k_{ex}$*ESA_EpoR_i"
4. "$k_t$*Bmax" and "$k_t$*EpoR"
5. "$k_{di}$*ESA_EpoR_i"
6. "$k_{de}$*ESA_EpoR_i"
7. "$k_{clear}$*ESA"
8. "$k_{scout}$*ESA_SC"
9. "$k_{scclear}$*ESA_SC/($k_{scclearsat}$+ESA_SC)"
10. "$k_{hb\_pro}$*ESA_EpoR"
11. "$k_{hb\_deg}$*Hb"

Model Calibration

For calibration of the model parameters, the inventors used the D2D software package (Raue et al. PloS ONE 2013) in MATLAB (Release 2012b, The MathWorks, Inc., Natick, Mass., USA). In order to minimize the distance between the simulated model trajectories and the measured data, a maximum likelihood approach was applied. The inventors used a deterministic optimization algorithm combined with multiple starting points in the high dimensional parameter space to find the global optimum of the negative log-likelihood. As the parameter values can range over several orders of magnitude and are, by its biochemical definition, strictly positive, the optimization was performed in logarithmized parameter space. To account for the log-normally distributed measurement noise of protein time course data (Kreutz et al. Bioinformatics 2007), also the data were transformed onto the logarithmic scale and an additive error model was fitted simultaneously with the kinetic model parameters. (Raue et al. PloS ONE 2013)

The affinity parameters ($k_{on}$, $k_{off}$ or $k_{on}$ and $k_D$) and the number of binding sites ($B_{max}$) were estimated individually for each experimental condition, i.e. combination of ESA and cell type, as they depend on the biochemical properties of the ESA and on the EpoR expression level of the respective cell type.

The structural and practical identifiability of the parameters was analyzed using the profile likelihood approach as described by Raue et al. (Bioinformatics 2011). Furthermore, this method enabled the inventors to determine the parameter's confidence intervals and the uncertainties of the model predictions.

Example 1: Model Based Determination of ESA Binding Properties

To assess the role of Epo and Epo derivatives in the context of lung cancer, it was essential to develop a reliable, quantitative assay that enables to determine the number of binding sides per cell and the specific binding properties of different human ESA (Epo alpha, Epo beta, NESP and CERA). The inventors utilized our knowledge that rapid ligand depletion is characteristic for the Epo-EpoR system (Becker et al 2010) and established a robust ELISA assay to monitor Epo removal from cellular supernatants.

As shown in FIG. 1a this enabled us to accurately quantify the depletion of Epo alfa and Epo beta by murine BaF3 cells stably expressing the murine EpoR (BaF3-mEpoR) whereas parental BaF3 cells had no impact underscoring the specificity of the assay. These quantifications in combination with our dynamic pathway model of Epo-EpoR interactions (Becker et al 2010) enabled to calculate the dissociation constant $K_D$ (FIG. 1a) as well as the association rate $k_{on}$, the dissociation rate $k_{off}$ and the number of binding sides ($B_{max}$) for Epo alfa and Epo beta interaction with the murine EpoR.

Figure 1B:
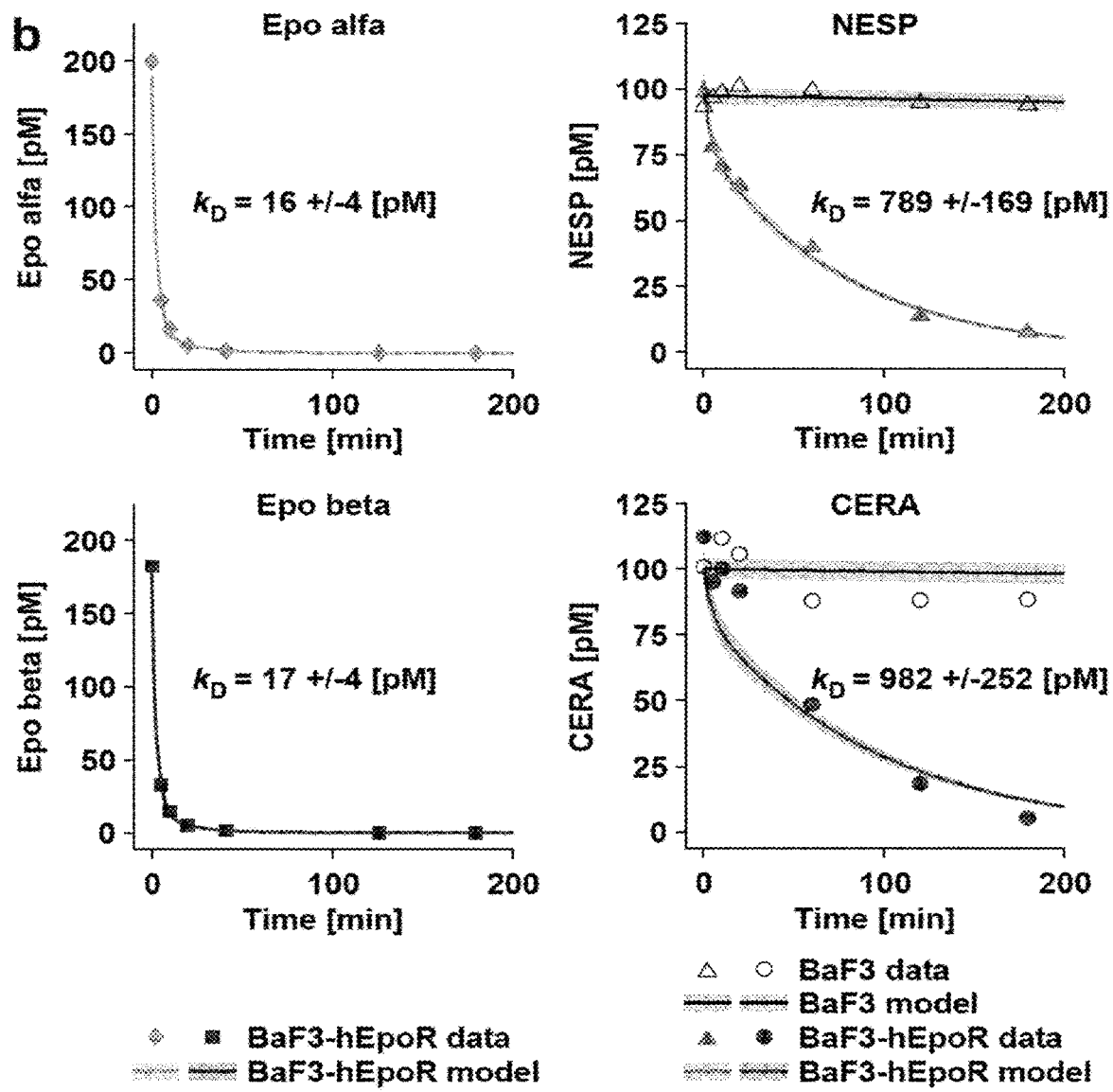

The estimated $B_{max}$ was in good agreement with the results obtained by traditional saturation binding assays using radioactively labelled ligand, further validating the assay. To comparatively examine the binding properties of different ESAs for the human EpoR, the inventors measured ESA depletion by BaF3 cells stably expressing the human EpoR (BaF3-hEpoR) or parental BaF3 cells (FIG. 1b). The results showed that whereas Epo alpha and Epo beta are very rapidly depleted, depletion of NESP and CERA is moderate. The quantitative time-resolved data in combination with our dynamic pathway model of ligand-receptor interaction enabled us to calculate that $K_D$ of Epo alpha and Epo beta, respectively, are with 16 and 17 pM very similar. However, for NESP the model indicates a $K_D$ of 789 pM and for CERA a KD of 982 pM suggesting for both Epo derivatives a much elevated dissociation constant.

Figure 1C:
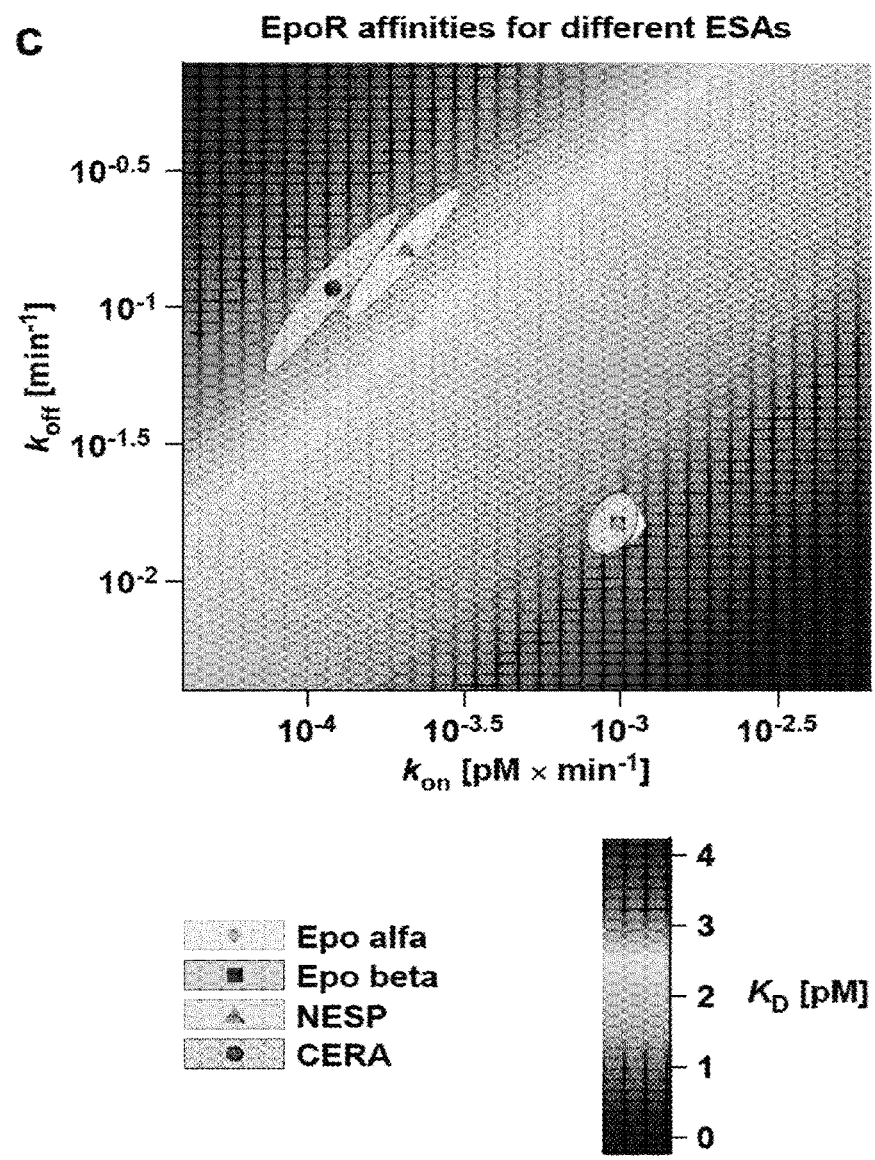

Relating the $K_D$ of the different ESA to the respective association and dissociation rates as shown in FIG. 1c reveals that the association of NESP and CERA is much slower compared to Epo alpha and Epo beta whereas the dissociation rate is enhanced. Therefore by combining simple time-resolved quantification of the concentration of Epo in cell supernatants with our dynamic pathway model it was possible to reliably determine the binding properties of ESA and to show that the available ESA differ significantly in their properties to bind to the human EpoR.

Example 2: Presence of Functional EpoR in NSCLC Cell Lines

Figure 2A:
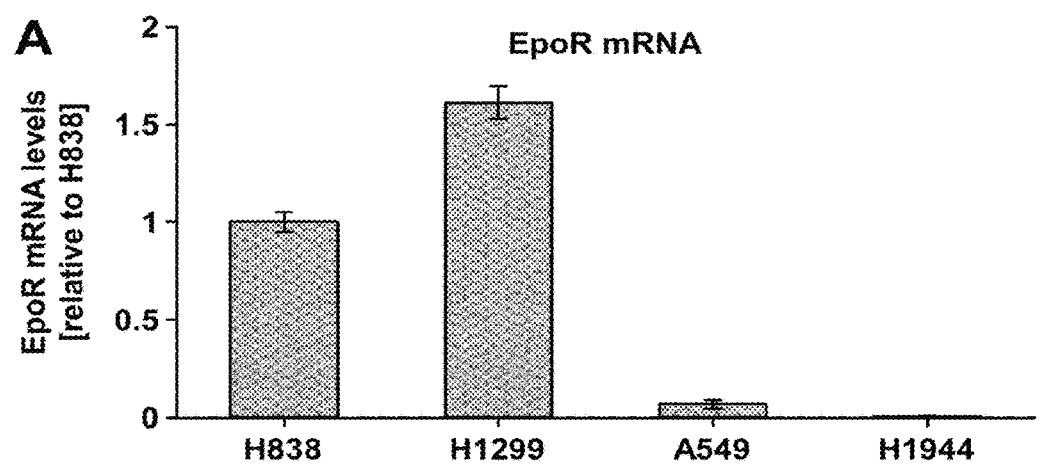
Figure 2B:
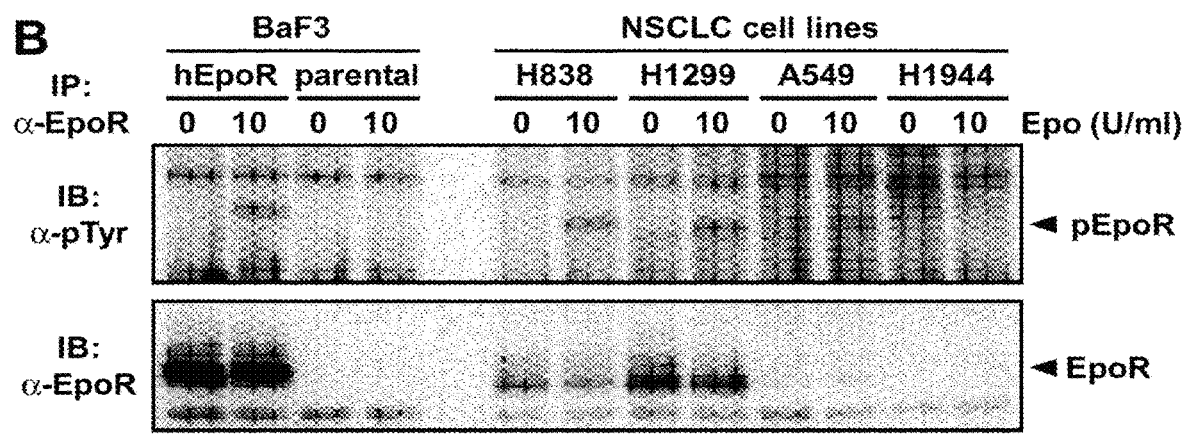
Figure 2C:
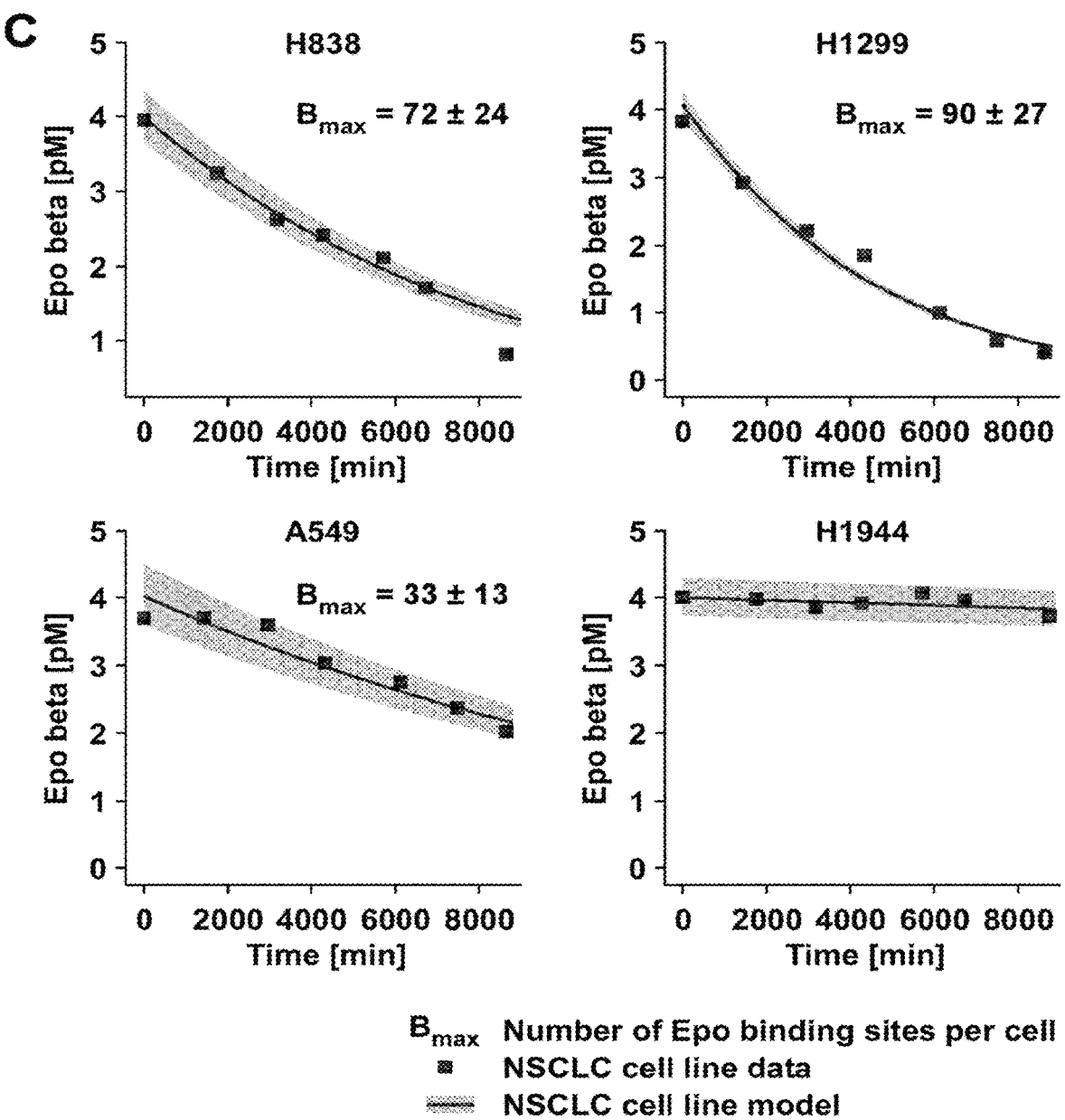

To determine the presence of a functional EpoR in lung cancer cells, the inventors first screened a panel of NSCLC cell lines for the presence of EpoR mRNA. Among these we identified three adenocarcinoma NSCLC cell lines that showed significant levels of EpoR mRNA transcripts. As depicted in FIG. 2a H838 and H1299 showed moderate expression levels of EpoR mRNA and A549 low levels. H1944 represent NSCLC cell lines with levels below the detection limit (FIG. 2a). Next evaluated was the expression of the EpoR protein in the four selected NSCLC cell lines as well as its functionality. Enrichment by immunoprecipitation and detection by immunoblotting revealed the presence of the EpoR protein in H838 and H1299 and at very low levels in A549, whereas it was absent in H1944 (FIG. 2b). In line with previous observations the overall expression level of EpoR protein was very low compared to BaF3-hEpoR.

Upon stimulation with Epo as expected the tyrosine phosphorylated form of the receptor was absent in parental BaF3 cells and H1944, but evident in H838, H1299 and A549 indicating the presence of a signaling competent, functional EpoR in these three NSCLC cell lines. To determine the binding properties of the EpoR expressed in the NSCLC cell lines, the inventors applied the depletion assay and showed (FIG. 2c) that Epo beta was depleted by the NSCLC cell lines harboring a functional EpoR, but not by the EpoR negative NSCLC cell line H1944 (FIG. 1b). However, Epo beta depletion was much slower compared to BaF3-EpoR cells suggesting the presence of a significantly lower number of cell surface receptors. Accordingly, analysis of the time-resolved data with the dynamic pathway model revealed binding sides ranging from undetectable to 90 per cell (FIG. 2c and Table 2), yet the estimated $K_D$ was comparable to the estimates with BaF3-hEpoR. This shows that ligand depletion and signaling competent receptor is present on a subset of NSCLC cell lines.

Example 3: EpoR Depletion Kinetics in Cells with High Numbers of EpoR

The main target of Epo treatment during anemia are erythroid progenitor cells at the colony forming units-erythroid (CFU-E) stage that express high levels of the EpoR. To quantify the cell surface expression of the EpoR on human CFU-E and characterize the binding properties, human CD34+ hematopoietic stem cells (hHSC) were prepared from human umbilical cord blood and differentiated to human CFU-E (hCFU-E). Time-resolved analysis of Epo beta depletion revealed rapid reduction of Epo beta from the supernatants of hCFU-E but not of hHSC that lack the EpoR (FIG. 3a). Model based analysis showed a $K_D$ comparable to BaF3-hEpoR and a $B_{max}$ of 365 binding sites per cell that was one order of magnitude lower compared to BaF3-hEpoR but one order of magnitude higher in comparison to the NSCLC cell line H838.

To examine whether some of the available ESA could have advantages in the tumor context due to the distinct binding properties, the inventors aimed at establishing a cell model system with elevated hEpoR expression levels mimicking the situation in hCFU-E as hCFU-E are only available at extremely limiting amounts. The inventors stably expressed the hEpoR in H838 (H838-hEpoR) and showed by enrichment using immunoprecipitation and immunoblotting that the expression of the EpoR was highly increased and the phosphorylated EpoR was substantially elevated (FIG. 3b). Depletion experiments and model-based analysis revealed binding properties rather similar to hCFU-E (FIG. 3c) establishing the H838-hEpoR cell line as suitable model system to examine the impact of different ESA on cells harboring high levels of the EpoR as observed in the hematopoietic system versus cells expressing low levels as in the tumor context.

Figure 4A:
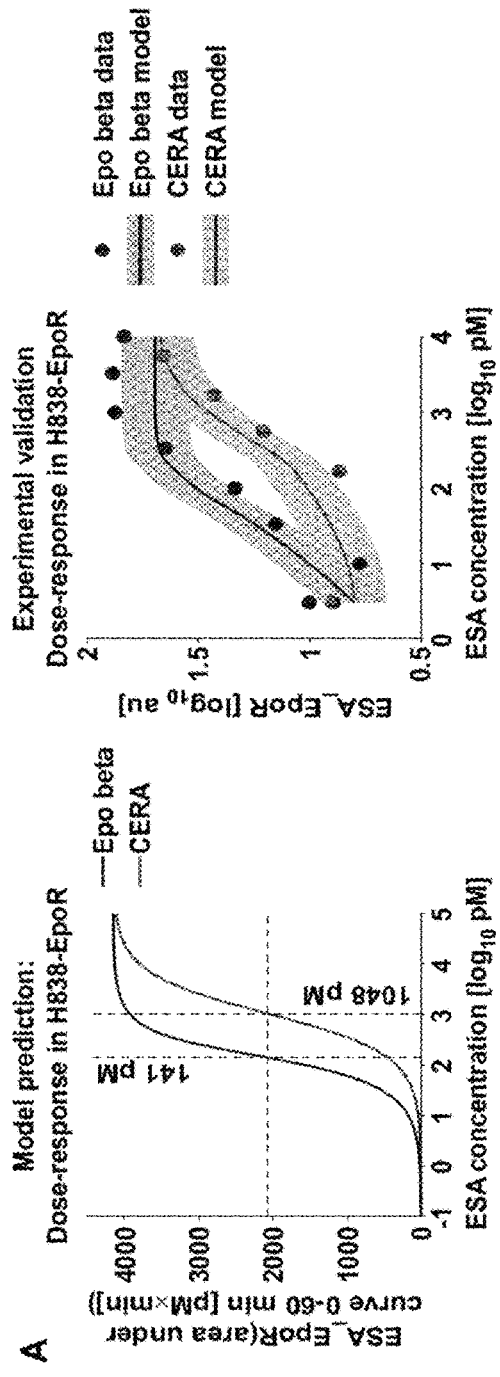

Example 4: Identification of CERA as an ESA Preferentially Activating Cells with High EpoR Expression To compare the impact of ESA on tumor cells that express low levels of EpoR versus cells that display elevated EpoR levels such as H838-EpoR, model simulations were performed. As readout for EpoR signaling, we calculated the integral of ESA bound to the EpoR (ESA_EpoR) for the first 60 minutes after stimulation. First these stimulations were performed for different ESA concentrations and predicted the $EC_{50}$ for both Epo beta and CERA in cells with high EpoR levels (FIG. 4a). The model predicts that a 10-fold higher concentration of CERA is required for the same activation. This model prediction was experimentally validated in H838-EpoR cells by quantitative immunoblotting against phosphorylated EpoR.

Figure 4B:
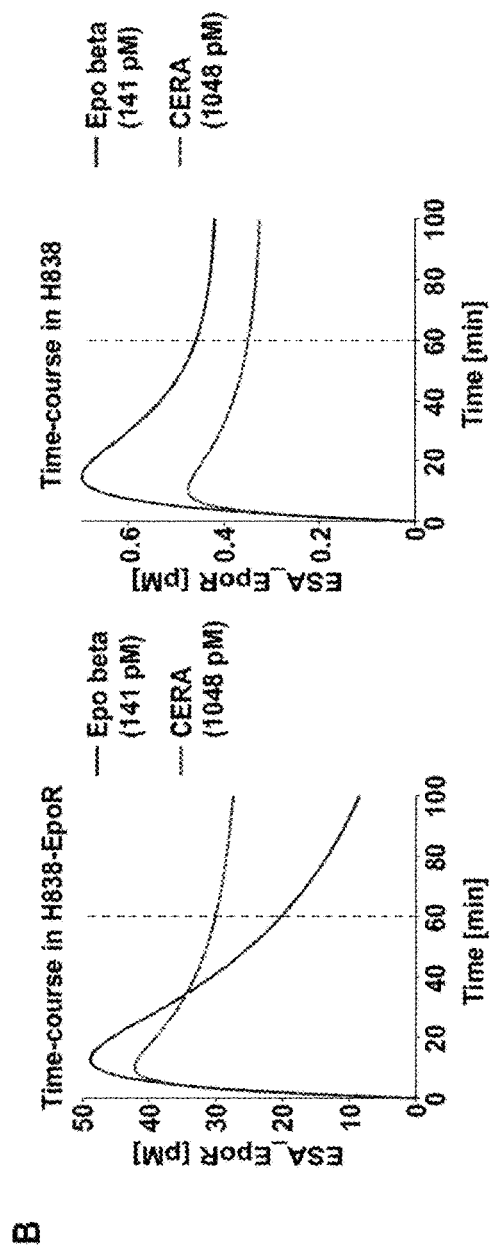

Interestingly, the model predicted that the ESA concentrations that induce the same activation in cells with high EpoR levels act differently in cells with low levels of EpoR such as H838. As these cells deplete less Epo beta, Epo beta results in stronger activation than CERA in cells with low levels of EpoR (FIG. 4b). Experimentally this model prediction was validated in H838 cells by quantitative mass spectrometry against phosphorylated STAT5. Thus, CERA was identified as an ESA preferentially activating cells with high EpoR expression, such as H838-EpoR and hCFU-E cells, rather than cells with low EpoR expression, such as NSCLC cells.

Example 5: Determination of the Number of CFU-E Cells in Healthy Subjects and NSCLC Patients by an Integrated PK/PD Model Having identified CERA as an ESA preferentially acting on cells with high EpoR levels, we integrated our model with pharmacokinetic (PK) data to describe CERA dynamics in patients (the integrative (PK/PD) ESA-EpoR mathematical model; see above). In a first step, the inventors analyzed mean PK values of CERA in the serum of healthy subjects (Locatelli et al.) as well as of NSCLC stage IIIB-IV patients (Hirsh et al). As CERA, which is pegylated, is not cleared by the kidney, it was hypothesized that the clearance of CERA in the blood stream is only accomplished by binding to EpoR and internalization, as seen in the in vitro experiments. Furthermore, it was assumed that the main difference between healthy subjects and NSCLC patients in Epo dynamics is the number of CFU-E cells, which may be reduced by the tumor load and by the chemotherapy. Indeed, these assumptions were sufficient to describe the experimental PK data for both healthy subjects and cancer patients (FIG. 5a). Furthermore, the model determined a decrease of 72% in the average number of CFU-E cells in the NSCLC stage IIIB-IV patients, resulting in longer clearance times of CERA.

Then, the inventors applied the same approach to PK data of individual NSCLC patients. While the data appears very heterogeneous, the model could again describe all data sets based only on different numbers of ESA binding sites, i.e. CFU-E cells. While ESA binding sites may also be present on other cells, such as the NSCLC cells, they will not contribute significantly to clearance of CERA due to their low expression levels. Importantly, it was possible to determine the number of CFU-E cells for each cancer patient, showing a high patient-to-patient variability (FIG. 5c).

Example 6: Determination of the Number of CFU-E Cells in Healthy Subjects and NSCLC Patients Based on the Patient Hemoglobin (Hb) Levels The above model was also able to correlate the hemoglobin (Hb) increments with the PK/PD data in individualized patient data sets. The PK profiles correlates with the number of CFU-E and this number with the recovery of the anemia, indicated by Hb levels. The inventors established the correlation between the individual patient histories with the PK profiles and these ones with the number of CFU-E per patients, and these ones with the outcome of the ESA treatment (increment of Hb levels). The Hb model includes therefore the additional reactions (FIG. 6c) of the production of Hb by active ESA-EPO-R signalling since the ESA-EPO-R signalling induces the maturation of erythrocytes that therefore increases Hb concentrations. Additionally, the model includes the patient specific degradation of Hb, which is easily determined in anemic patients, because there Hb status is regularly monitored.

Example 7: CERA Preferentially Activates Cells with High EpoR Expression

We examined the impact of ESA binding properties and of different ESA binding sites on receptor activation to assess whether some of the available ESAs could have advantages in the tumor context. The ESA-EpoR mathematical model predicted that ESA concentrations that induce the same degree of activation of signaling in cells with high EpoR abundance act differently in cells with low levels of the EpoR (FIGS. 4a and 4b). This behavior was experimentally validated in H838 and hCFU-E cells by mass spectrometric analysis of STAT5 phosphorylation in response to stimulation with Epo beta or CERA (FIG. 7). H838 and hCFU-E were stimulated with 1331 pM of Epo beta or 8841 pM of CERA, concentrations that correspond to the half-maximal activation of STAT5 phosphorylation in hCFU-Es. As the ESA-EpoR mathematical model predicted (FIG. 4), the activation of EpoR signaling by CERA is less effective in cells with low levels of the EpoR such as NSCLC cells (FIG. 7 left panel) compared to cells with higher levels of the EpoR like hCFU-E (FIG. 7 right panel). Thus, we identify CERA as an ESA preferentially activating erythroid progenitor cells rather than tumor cells.

Figure 8A:
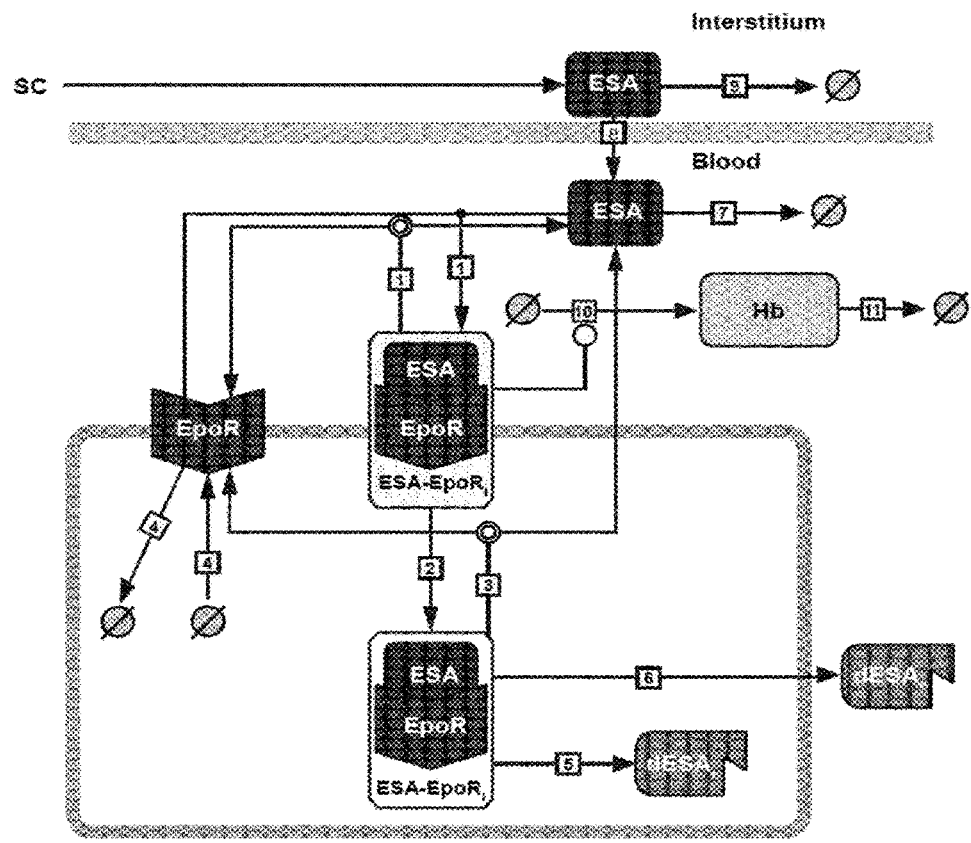
Figure 8B:
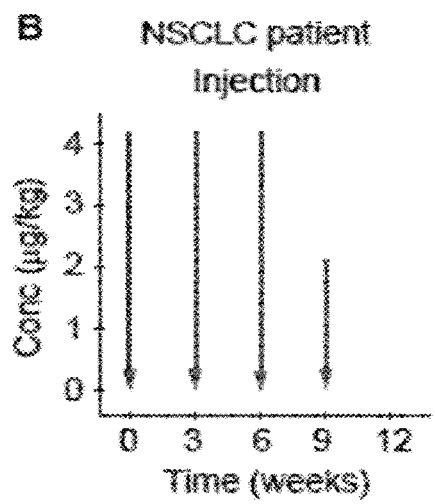
Figure 8B:
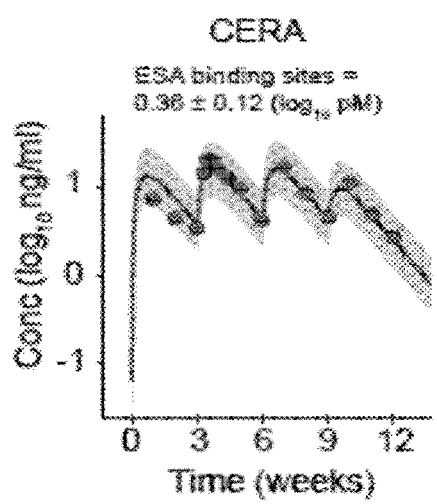
Figure 8B:
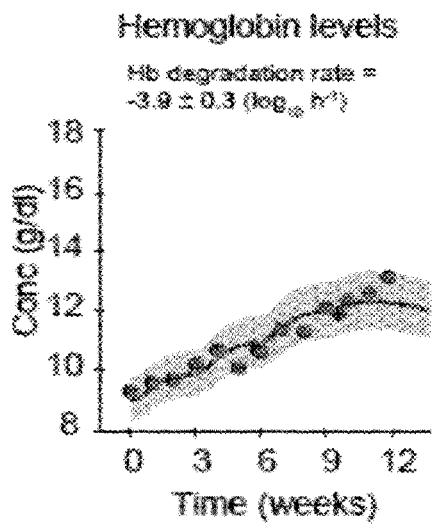
Figure 8C:
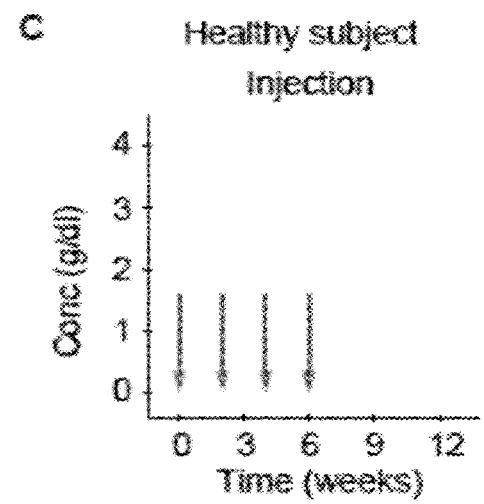
Figure 8C:
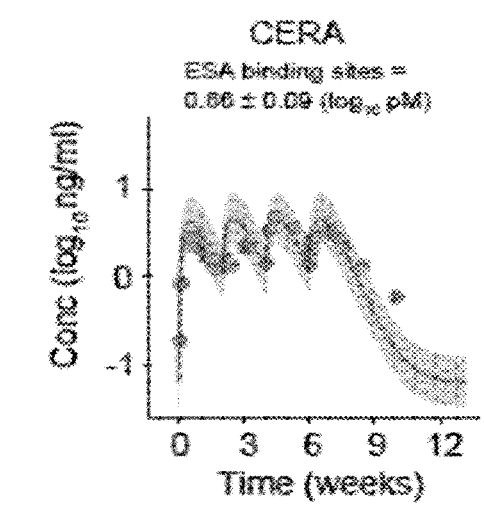
Figure 8C:
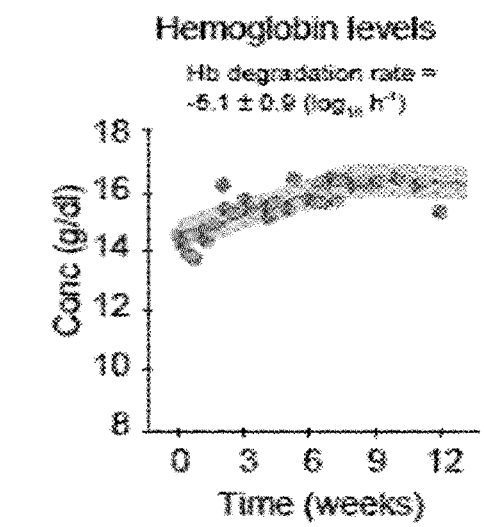

Example 8: Integrative PK/PD ESA-EpoR Model-Based Stratification of NSCLC Patients As in example 5, we applied the same approach to the PK/PD data from individual NSCLC patients (clinical trial CSR NA17101) and healthy subjects (clinical trial WP16422). Although the patient data is apparently very heterogeneous, the integrative PK/PD ESA-EpoR model (FIG. 8a) is able to describe all patient data sets. Herein we exemplify two individual cases, NSCLC patient ID:2101 (clinical trial CSR NA17101) (FIG. 8b) and healthy subject ID:25 (clinical trial WP16422) (FIG. 8c). The integrative PK/PD ESA-EpoR model was able to describe the time-course of CERA concentrations determined in the serum and the corresponding Hb levels measured in the blood in response to the indicated ESA regimen, (FIGS. 8b and c). To describe the heterogeneous PK/PD data, we assume that in addition to the different number of ESA binding sites, already explained in example 5, the net loss of Hb (KHb_deg) could be another key difference between healthy subjects and NSCLC patients. Due to the inflammation associated with cancer, the half-life of erythrocytes is shortened and could therefore affect the KHb_deg in particular in cancer patients. Indeed, this assumption was sufficient to describe the experimental PD data for both cancer patients and healthy subjects (FIGS. 8b and c lower panels).

Figure 8D:
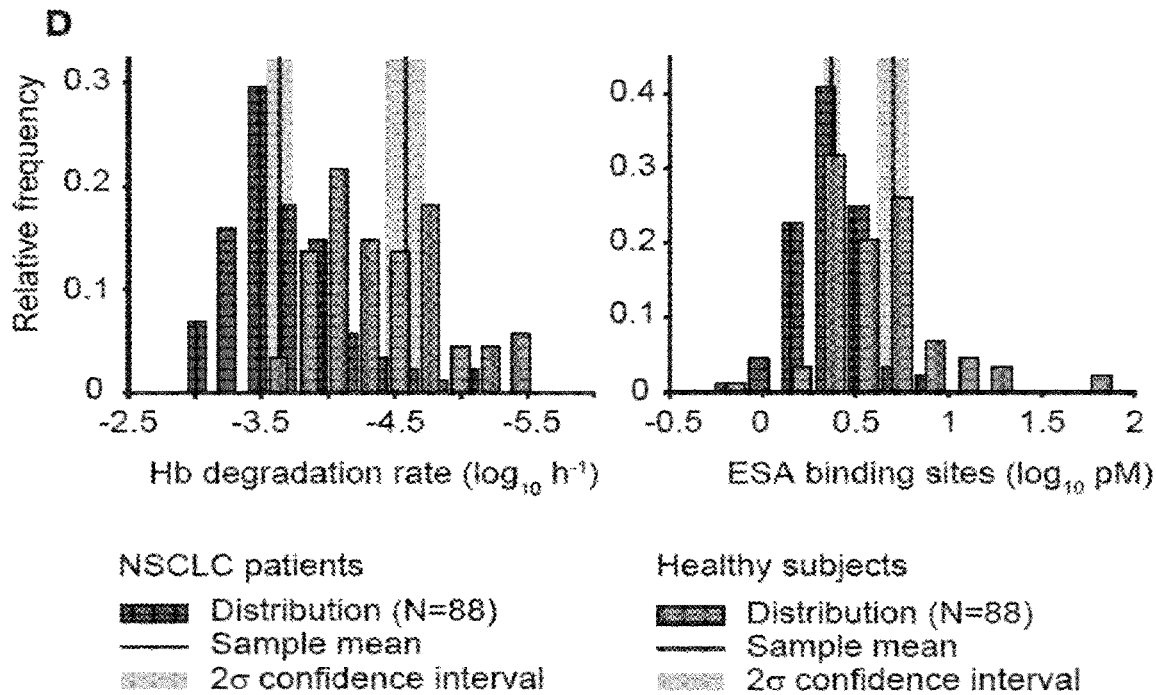

Importantly, we can estimate the number of ESA-binding sites for individual cancer patients, showing a high patient-to-patient variability and a very different distribution from the healthy subjects (FIG. 8d right). Further, the distribution of the estimated KHb_deg parameter differs widely in healthy subjects and NSCLC patients (FIG. 8d left panel).

Example 9: Model-Based Treatment Optimization in NSCLC Anemia

Figure 9A:
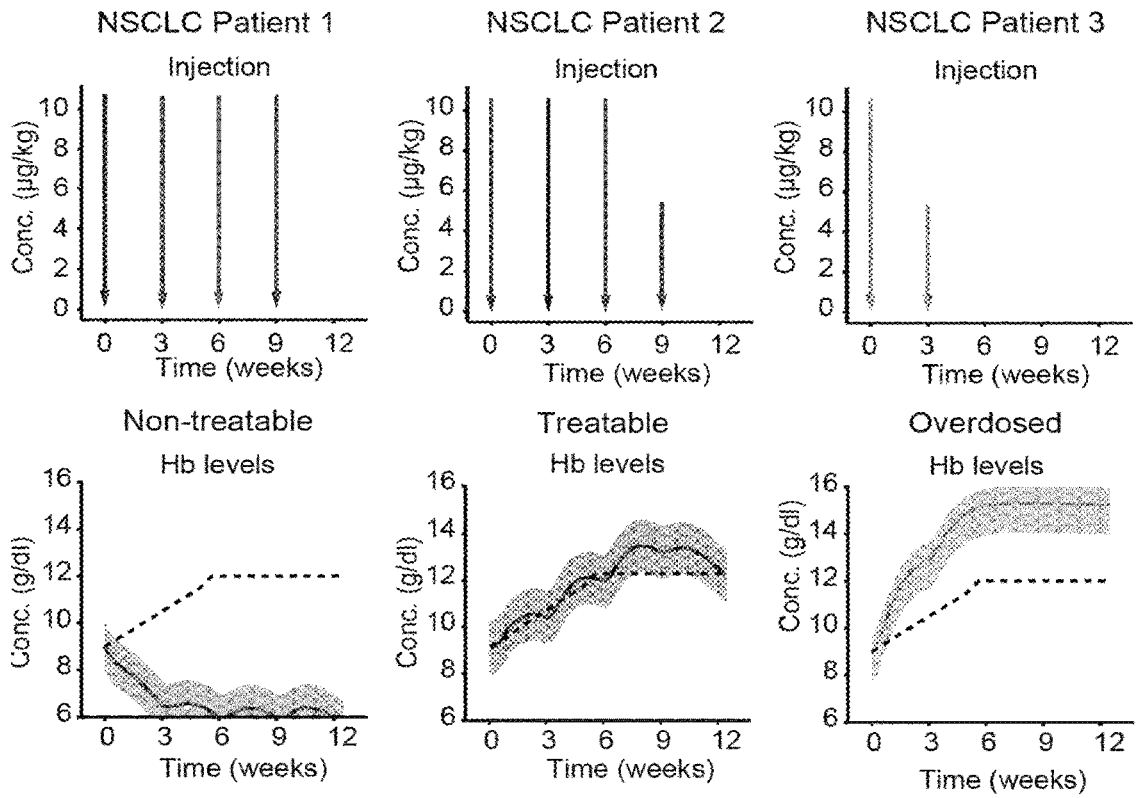

The current guidelines defined by the European Medicines Agency (EMEA) recommend that the hemoglobin (Hb) response to ESA treatment of anemia in cancer should neither exceed increments of Hb≥2 g/dl in the following four weeks after the first ESA dose nor should Hb levels reach higher values than 13 g/dl. These guidelines recommend doubling the ESA dose if there is no response to the treatment (Hb increments ≤1 g/dl in 4 weeks after the first ESA dose), or reducing the ESA dose by 25% or 50% if the increment of Hb levels is ≥2 g/dl after four weeks and/or if Hb values ranging from 12 g/dl to 13 g/dl are reached. Interruption of the treatment is mandatory if the Hb value is higher than 13 g/dl. We employed the integrative PK/PD ESA-EpoR mathematical model to calculated the EC50 (ESA concentration required to obtain half-maximum EpoR occupancy) for each ESA and determined the CERA doses that correspond to the current guidelines for NESP. Considering the EMEA-recommended ESA guidelines, we performed CERA treatment simulations based on the patient-specific parameters in three NSCLC patients (FIG. 9a). In the case of Patient 1 (ID:2303 CSR NA17101) the maximum CERA dose (equivalent to maximal NESP dose in the guidelines) would be given every three weeks (FIG. 9a upper left panel), and the model predicts no response within the current ESA guidelines (FIG. 9a lower left panel). In Patient 2 (ID:1022 CSR NA17101) the model predicts a fast hematological response within the current ESA guidelines (FIG. 9a upper and lower middle panels). In Patient 3 (ID:2652 CSR NA17101) the model predicts an interruption of the ESA treatment (FIG. 9a upper right panel) due to overshooting Hb values in response to the treatment within the current ESAs guidelines (FIG. 9a lower right panels).

Figure 9B:
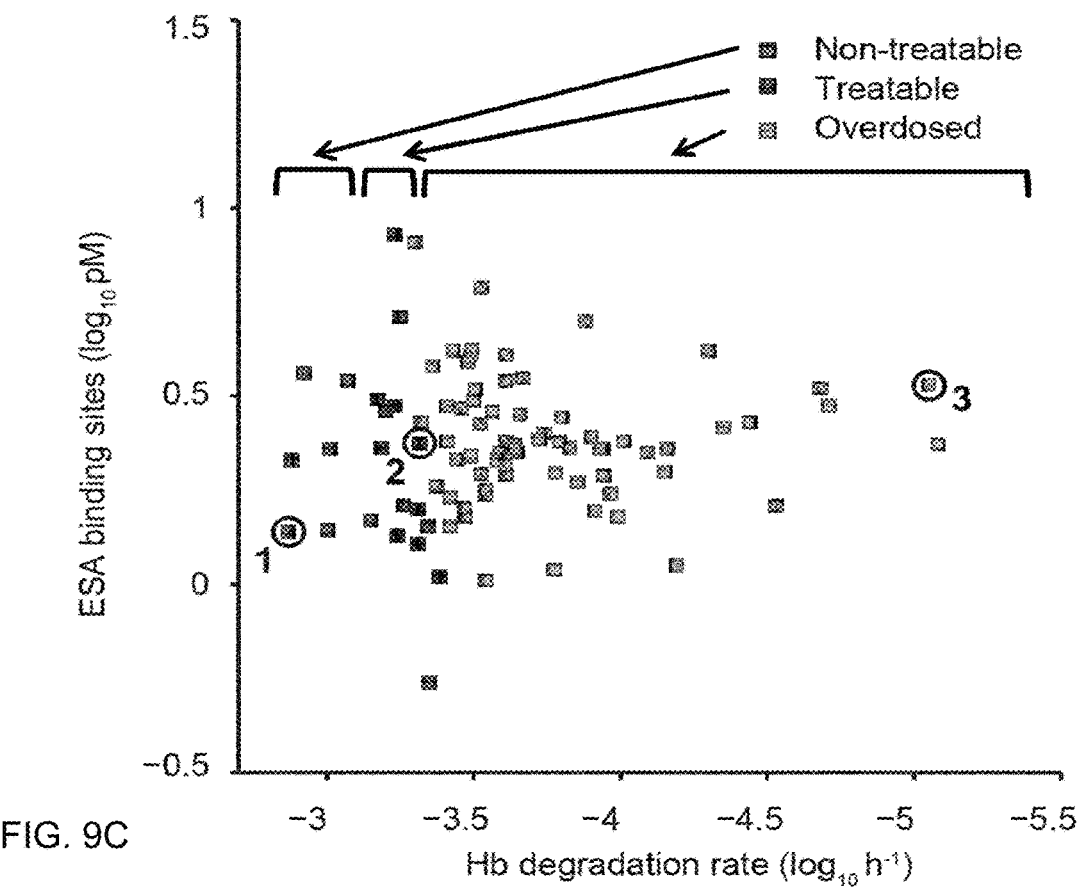

To understand the impact of the current ESA guidelines in the NSCLC anemia treatment, 88 patients from the CSR NA17101 clinical trial were plotted based on patient-specific ESA binding sites and the Hb degradation rates. Patient stratification was carried out by response prediction within the current EMEA-recommended ESA guidelines (FIG. 9b). We defined as overdosed patients that were predicted to have an Hb increment >2 g/dl in four weeks and/or reaching Hb levels >13 g/dl, such as Patient 3 (ID:2652 CSR NA17101). We defined patients as treatable if they were predicted to have an Hb increment of ≤2 g/dl in four weeks and reach Hb levels of 12 g/dl, such as Patient 2 (ID:1022 CSR NA17101). We defined patients as non-treatable if they are predicted to have no increment of Hb levels during the treatment, such as Patient 1 (ID:2303 CSR NA17101). Interestingly, the integrative PK/PD ESA-EpoR mathematical model predicted a systematic overdosing of a large fraction of NSCLC IIIB-IV patients treated within the EMEA-recommended ESA guidelines for anemia in cancer (FIG. 9b).

Figure 9C:
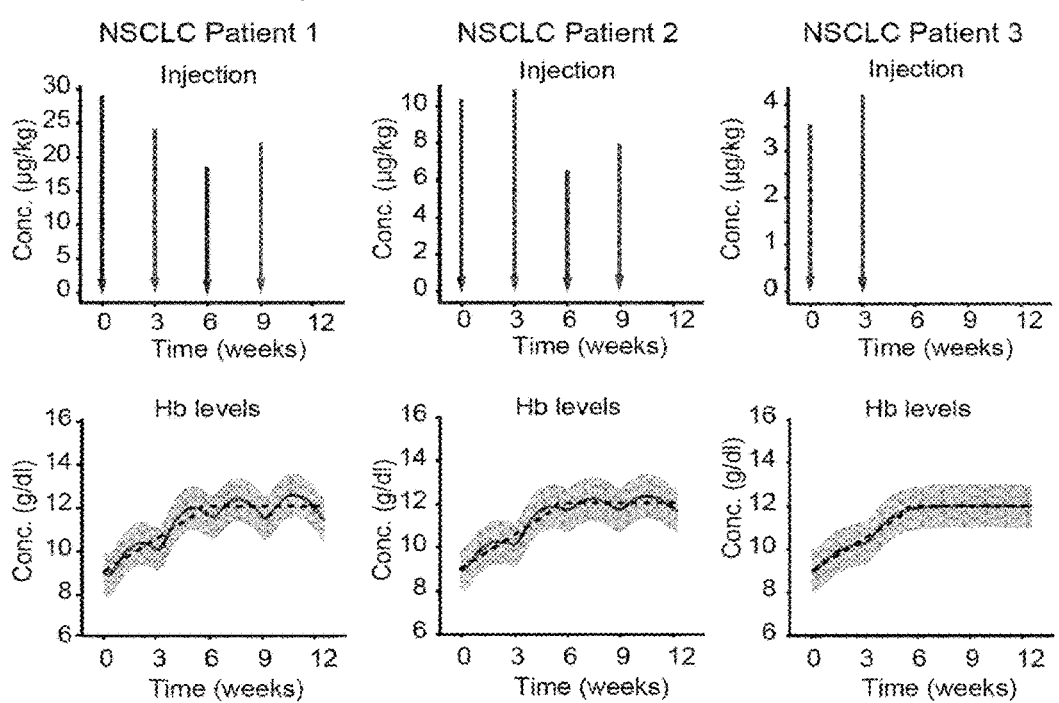
Figure 9D:
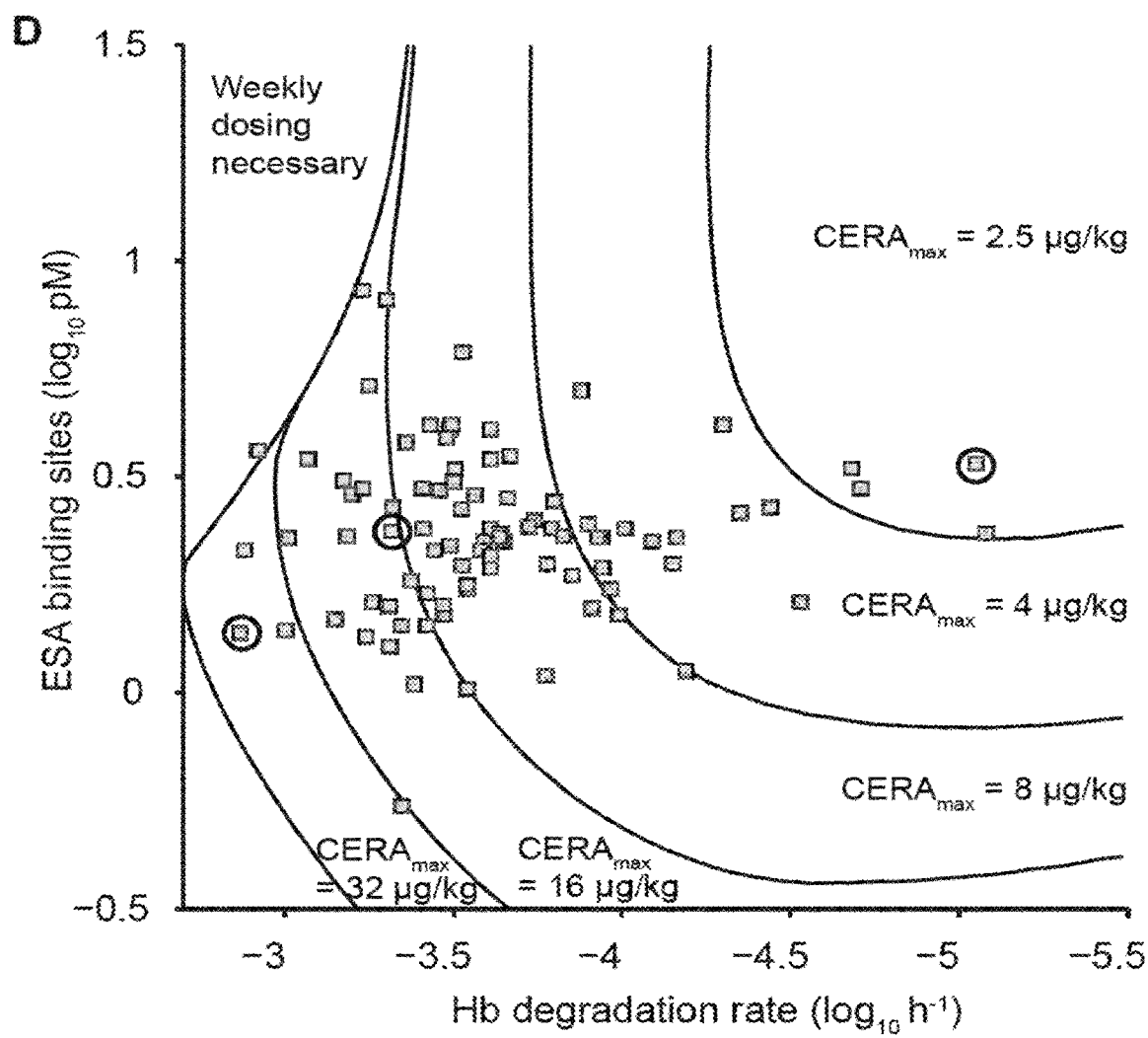

The integrative PK/PD ESA-EpoR mathematical model can optimize the ESA dosing and scheduling to achieve a hematological response within the limits of the ESAs guidelines for most of the NSCLC IIB-IV patients, minimizing the risk of overdosing (FIG. 9c). For Patient 2 and 3, the model is able to optimize the ESA regimens (FIG. 9c middle and right upper panel) that result in hematological responses without compromising the safety limits (FIG. 9c middle and right lower panels). In the particular case of Patient 1, the model recommended an ESA regimen beyond the ESA guidelines (FIG. 9c left upper panel) to achieve a hematological response (FIG. 9c left lower panel). Finally, we displayed the prediction for all ESA regimens required to effectively treat all the NSCLC IIIB-IV patients of the CSR NA17101 clinical trial (FIG. 9d).

The invention claimed is:

1. A method for determining a dosage of an Erythropoiesis Stimulating Agent (ESA) that is sufficient for treating anemia in a patient, the method comprising the steps of:
   a) Calculating a degradation of hemoglobin per time for the patient from a hemoglobin concentration of the patient from at least two separate time points;
   b) Determining in vitro a present hemoglobin concentration of the patient from a concentration of hemoglobin from a recent blood sample obtained from the patient;
   c) Calculating an ESA dosage based on the degradation of hemoglobin per time and the present hemoglobin concentration to treat anemia in the patient;
   d) Administering the ESA dosage to the patient to thereby treat anemia in the patient;
   e) Monitoring the clearance of said ESA dosage from a serum in said patient;
   f) Calculating from the clearance of said ESA dosage in said patient the number of initial ESA binding sites present in said patient using a non-linear dynamic pharmacokinetic (PK) ESA-EPO-R pathway model; and
   g) Adjusting the ESA dosage administered to the patient in accordance with the number of ESA binding sites.

2. The method according to claim 1, wherein the hemoglobin concentration of the patient from at least two separate time points is determined by measuring the hemoglobin concentrations in blood samples obtained from the patient from at least two different time points, or from a past anemia treatment history of the patient.

3. The method of claim 1, further including the step of:
   Monitoring the hemoglobin concentration of the patient over time after the administration of the ESA dosage.

4. The method of claim 3, wherein the hemoglobin concentration of the patient is monitored by obtaining a blood sample from the patient.

5. The method of claim 1, wherein the administration is a subcutaneous or intravenous injection.

6. The method of claim 1, wherein the ESA dosage is administered subcutaneously, and wherein the non-linear dynamic pharmacokinetic (PK) ESA-EPO-R pathway model considers clearance of the administered ESA in a blood compartment, transport of the administered ESA from an interstitial compartment into the blood compartment, and clearance of the ESA in the interstitial compartment.

7. The method of claim 1, wherein the ESA dosage is selected from the group of an Epoetin alfa dosage, an Epoetin beta dosage, an erythropoiesis stimulating protein dosage and a Continuous erythropoietin receptor activator dosage.

8. The method of claim 1, wherein said non-linear dynamic pharmacokinetic (PK) ESA-EPO-R pathway model is based on a system of the ordinary differential equations (ODE):

$$\frac{d[ESA_{SC}]}{dt} = \qquad (2.1.)$$
$$-k_{sc_{clear}} \cdot [ESA_{SC}]/(k_{sc\_clear\_sat} + [ESA_{SC}]) - k_{sc\_out} \cdot [ESA_{SC}]$$

$$\frac{d[ESA]}{dt} = k_{sc_{out}} \cdot [ESA_{SC}] - k_{clear} \cdot [ESA] - \qquad (2.2.)$$
$$k_{on} \cdot [ESA] \cdot [EpoR] + k_{off} \cdot [ESAEpoR] + k_{ex} \cdot [ESAEpoR_i]$$

$$\frac{d[EpoR]}{dt} = -k_{on} \cdot [ESA] \cdot [EpoR] + \qquad (2.3.)$$
$$k_{off} \cdot [ESAEpoR] + k_t \cdot B_{max} - k_t \cdot [EpoR] + k_{ex} \cdot [ESAEpoR_i]$$

-continued $$\frac{d[ESAEpoR]}{dt} = k_{on} \cdot [ESA] \cdot [EpoR] - k_{off} \cdot [ESAEpoR] - k_e \cdot [ESAEpoR] \quad (2.4.)$$

$$\frac{d[ESAEpoRi]}{dt} = k_e \cdot [ESAEpoR] - k_{ex} \cdot [ESAEpoR_i] - k_{di} \cdot [ESAEpoR_i] - k_{de} \cdot [ESAEpoR_i] \quad (2.5.)$$

$$\frac{d[dESAi]}{dt} = k_{di} \cdot [ESAEpoR_i] \quad (2.6.)$$

$$\frac{d[dESAe]}{dt} = k_{de} \cdot [ESAEpoR_i], \quad (2.7.)$$

where,
ESA is Erythropoiesis-stimulating agent in medium/blood,
EpoR is Erythropoietin receptor,
ESA EpoR is a complex of ESA bound to EpoR on the cell surface,
$ESAEpoR_i$ is an internalized complex of ESA bound to EpoR,
$dESA_i$ is intracellular degraded ESA,
$dESA_e$ is extracellular degraded ESA,
$ESA_{sc}$ is ESA in the subcutaneous compartment,
$k_{sc\ clear}$ is ESA clearance in the subcutaneous compartment,
$k_{sc\ clear\ sat}$ is saturation of ESA clearance in the subcutaneous compartment,
$K_{sc\ out}$ is an ESA transportation constant to the blood compartment,
$k_{clear}$ is an ESA clearance constant in the blood compartment,
$k_{on}$ is an ESA-EpoR association rate/on-rate,
$k_{off}$ is an ESA-EpoR dissociation rate/off-rate,
$k_t$ is a ligand-independent receptor turnover rate,
$k_e$ is an ESA-EpoR complex internalization constant,
$k_{ex}$ is an ESA and EpoR recycling constant,
$k_{di}$ is an intracellular ESA degradation constant,
$k_{de}$ is an extracellular ESA degradation constant,
and wherein $B_{max}$ is the number of initial ESA binding sites per cell/per patient.

* * * * *